(12) United States Patent
Campanella et al.

(10) Patent No.: US 12,036,589 B2
(45) Date of Patent: Jul. 16, 2024

(54) DEVICES AND TECHNIQUES RELATING TO LANDFILL GAS EXTRACTION

(71) Applicant: Loci Controls, Inc., Wareham, MA (US)

(72) Inventors: Andrew J. Campanella, Somerville, MA (US); Melinda Sims, Seattle, WA (US); Nathan Pallo, Somerville, MA (US); Ian Martin, Sharon, MA (US)

(73) Assignee: Loci Controls, Inc., Wareham, MA (US)

( * ) Notice: Subject to any disclaimer, the term of this patent is extended or adjusted under 35 U.S.C. 154(b) by 0 days.

(21) Appl. No.: 18/158,742

(22) Filed: Jan. 24, 2023

(65) Prior Publication Data
US 2023/0234112 A1    Jul. 27, 2023

Related U.S. Application Data

(63) Continuation of application No. 17/369,395, filed on Jul. 7, 2021, now Pat. No. 11,602,778, which is a
(Continued)

(51) Int. Cl.
*B09B 1/00*   (2006.01)
*E21B 43/12*  (2006.01)
*G01N 33/00*  (2006.01)

(52) U.S. Cl.
CPC ............ *B09B 1/006* (2013.01); *B09B 1/00* (2013.01); *E21B 43/12* (2013.01); *G01N 33/0004* (2013.01); *G01N 33/0047* (2013.01)

(58) Field of Classification Search
CPC .......... B09B 1/006; B09B 1/00; E21B 43/12; G01N 33/0004; G01N 33/0047; G01N 33/0063
See application file for complete search history.

(56) References Cited

U.S. PATENT DOCUMENTS 3,062,037 A   11/1962  Donner et al.
3,567,387 A    3/1971  Jones
(Continued)

FOREIGN PATENT DOCUMENTS

EP         0 743 515 A1   11/1996
WO    WO 2006/005014 A2   1/2006
(Continued)

OTHER PUBLICATIONS

U.S. Appl. No. 14/532,807, Campanella et al., filed Nov. 4, 2014.
(Continued)

*Primary Examiner* — James G Sayre
(74) *Attorney, Agent, or Firm* — Wolf, Greenfield & Sacks, P.C.

(57) ABSTRACT

Devices and techniques related to landfill gas extraction are disclosed. A technique for controlling extraction of landfill gas from a landfill through a gas extraction system is described. The method may include measuring a plurality of values indicating conditions associated with the landfill; computing, based at least in part on the plurality of values and on a model of the landfill, a predicted future state of the landfill; determining, based at least in part on the predicted future state of the landfill, one or more control parameters for one or more respective control devices configured to control operation of the gas extraction system; applying the one or more control parameters to the one or more respective control, and with the one or more control devices, controlling extraction of the landfill gas from the landfill based, at least in part, on the one or more respective control parameters.

20 Claims, 7 Drawing Sheets

Related U.S. Application Data continuation of application No. 16/831,131, filed on Mar. 26, 2020, now Pat. No. 11,084,074, which is a continuation of application No. 15/456,936, filed on Mar. 13, 2017, now Pat. No. 10,639,687, which is a continuation of application No. 14/532,807, filed on Nov. 4, 2014, now Pat. No. 10,029,290.

(60) Provisional application No. 61/913,628, filed on Dec. 9, 2013, provisional application No. 61/899,828, filed on Nov. 4, 2013.

(56) References Cited

U.S. PATENT DOCUMENTS

| | | |
|---|---|---|
| 4,026,355 A | 5/1977 | Johnson et al. |
| 4,191,541 A | 3/1980 | Jenkins |
| 4,226,675 A | 10/1980 | Lewis et al. |
| 4,227,897 A | 10/1980 | Reed |
| 4,494,380 A | 1/1985 | Cross |
| 4,499,378 A | 2/1985 | Miyatake et al. |
| 4,670,148 A | 6/1987 | Schneider |
| 4,890,672 A | 1/1990 | Hall |
| 5,063,519 A | 11/1991 | Zison |
| 5,209,941 A | 5/1993 | Wuest |
| 5,223,229 A | 6/1993 | Brucker |
| 5,239,861 A | 8/1993 | Fujita et al. |
| 5,451,249 A | 9/1995 | Spiegel et al. |
| 5,458,006 A | 10/1995 | Roqueta |
| 5,665,314 A | 9/1997 | Berger et al. |
| 5,681,360 A | 10/1997 | Siwajek et al. |
| 5,695,641 A | 12/1997 | Cosulich et al. |
| 5,830,262 A | 11/1998 | Marchini et al. |
| 6,169,962 B1 | 1/2001 | Brookshire et al. |
| 6,196,324 B1 | 3/2001 | Giacomino et al. |
| 6,241,950 B1 | 6/2001 | Veelenturf et al. |
| 6,399,391 B1 | 6/2002 | Tomlin |
| 6,591,695 B1 | 7/2003 | Brookshire et al. |
| 6,595,287 B2 | 7/2003 | Fisher |
| 6,611,760 B2 | 8/2003 | Bentley et al. |
| 6,749,368 B2 | 6/2004 | Ankeny et al. |
| 6,799,477 B2 | 10/2004 | Brookshire et al. |
| 6,999,883 B1 | 2/2006 | Brady et al. |
| 7,187,299 B2 | 3/2007 | Kunerth et al. |
| 7,198,433 B2 | 4/2007 | Augenstein et al. |
| 7,243,730 B2 | 7/2007 | Casey |
| 7,273,098 B2 | 9/2007 | Evans et al. |
| 7,373,976 B2 | 5/2008 | Casey |
| 7,387,163 B2 | 6/2008 | Seegers et al. |
| 7,448,828 B2 | 11/2008 | Augenstein et al. |
| 7,748,450 B2 | 7/2010 | Mundell |
| 7,866,921 B2 | 1/2011 | Stamoulis |
| 7,950,464 B2 | 5/2011 | Atencio et al. |
| 7,972,082 B2 | 7/2011 | Augenstein et al. |
| 8,047,276 B2 | 11/2011 | Stamoulis |
| 8,168,121 B2 | 5/2012 | Elkins |
| 8,186,211 B2 | 5/2012 | Boult et al. |
| 8,840,708 B1 | 9/2014 | Morrow et al. |
| 8,924,029 B2 | 12/2014 | Nath et al. |
| 9,062,536 B2 | 6/2015 | Fischer et al. |
| 10,029,290 B2 | 7/2018 | Campanella et al. |
| 10,400,560 B2 | 9/2019 | Campanella et al. |
| 10,408,747 B2 | 9/2019 | Schlueter et al. |
| 10,449,578 B2 | 10/2019 | Campanella et al. |
| 10,556,259 B2 | 2/2020 | Campanella et al. |
| 10,576,514 B2 | 3/2020 | Campanella et al. |
| 10,576,515 B2 | 3/2020 | Campanella et al. |
| 10,639,687 B2 | 5/2020 | Campanella et al. |
| 10,682,678 B2 | 6/2020 | Campanella et al. |
| 10,705,063 B2 | 7/2020 | Campanella et al. |
| 10,882,086 B2 | 1/2021 | Quigley et al. |
| 10,946,420 B2 | 3/2021 | Quigley et al. |
| 11,007,555 B2 | 5/2021 | Campanella et al. |
| 11,067,549 B2 | 7/2021 | Campanella et al. |
| 11,072,006 B2 | 7/2021 | Campanella et al. |
| 11,084,074 B2 | 8/2021 | Campanella et al. |
| 11,235,361 B2 | 2/2022 | Quigley et al. |
| 11,273,473 B2 | 3/2022 | Quigley et al. |
| 11,484,919 B2 | 11/2022 | Quigley et al. |
| 11,491,521 B2 | 11/2022 | Quigley et al. |
| 11,602,777 B2 | 3/2023 | Campanella et al. |
| 11,602,778 B2 | 3/2023 | Campanella et al. |
| 2001/0005812 A1* | 6/2001 | Brookshire ............... B09B 1/00 702/6 |
| 2002/0101718 A1 | 8/2002 | Negishi |
| 2003/0000281 A1 | 1/2003 | Ketler et al. |
| 2004/0055359 A1 | 3/2004 | Ketler et al. |
| 2004/0121201 A1 | 6/2004 | Roche et al. |
| 2006/0034664 A1 | 2/2006 | Augenstein et al. |
| 2006/0251540 A1 | 11/2006 | Benning et al. |
| 2007/0224085 A1 | 9/2007 | Tooley |
| 2007/0225923 A1* | 9/2007 | Tooley ................ G05B 13/048 702/47 |
| 2007/0254196 A1 | 11/2007 | Richards et al. |
| 2008/0011248 A1 | 1/2008 | Cutlip et al. |
| 2008/0127726 A1 | 6/2008 | Elkins |
| 2009/0136298 A1 | 5/2009 | Augenstein et al. |
| 2010/0310733 A1 | 12/2010 | Hoffman |
| 2011/0061439 A1 | 3/2011 | Dong et al. |
| 2011/0061874 A1 | 3/2011 | Stamoulis |
| 2011/0081586 A1 | 4/2011 | McAlister |
| 2011/0132104 A1 | 6/2011 | Benson et al. |
| 2011/0198094 A1 | 8/2011 | Stamoulis |
| 2011/0231099 A1 | 9/2011 | Elkins |
| 2011/0272420 A1 | 11/2011 | Landess et al. |
| 2012/0191349 A1 | 7/2012 | Lenz et al. |
| 2012/0206715 A1 | 8/2012 | Laub |
| 2012/0287418 A1 | 11/2012 | Scherer et al. |
| 2013/0036811 A1 | 2/2013 | Boult |
| 2013/0180703 A1 | 7/2013 | Colby |
| 2013/0193325 A1 | 8/2013 | Phillips et al. |
| 2013/0247647 A1 | 9/2013 | Mahoney et al. |
| 2013/0334418 A1 | 12/2013 | Cowie et al. |
| 2014/0023576 A1 | 1/2014 | Yezerets et al. |
| 2014/0182846 A1 | 7/2014 | Fischer et al. |
| 2014/0284935 A1 | 9/2014 | Disbennett et al. |
| 2014/0338878 A1 | 11/2014 | Tessnow |
| 2015/0000426 A1 | 1/2015 | Mustang |
| 2015/0168274 A1 | 6/2015 | Sheffield |
| 2015/0226045 A1 | 8/2015 | Fischer et al. |
| 2015/0275632 A1 | 10/2015 | Fischer et al. |
| 2015/0330938 A1 | 11/2015 | Henson et al. |
| 2015/0354032 A1 | 12/2015 | Yuan et al. |
| 2015/0362468 A1 | 12/2015 | Gerhold |
| 2016/0011159 A1 | 1/2016 | Sekiya et al. |
| 2016/0025696 A1 | 1/2016 | Birks et al. |
| 2016/0033391 A1 | 2/2016 | Stroganov et al. |
| 2016/0123946 A1 | 5/2016 | Dufresne |
| 2016/0169826 A1 | 6/2016 | Youssi et al. |
| 2016/0209133 A1 | 7/2016 | Hu et al. |
| 2016/0237007 A1 | 8/2016 | Morrow et al. |
| 2016/0238494 A1 | 8/2016 | Chrin, II |
| 2016/0247183 A1 | 8/2016 | Foody |
| 2016/0287870 A1 | 10/2016 | Yip et al. |
| 2016/0377457 A1 | 12/2016 | Zhang et al. |
| 2017/0080762 A1 | 3/2017 | Guinart et al. |
| 2017/0122065 A1 | 5/2017 | Fischer et al. |
| 2017/0173505 A1 | 6/2017 | Dhingra et al. |
| 2017/0176590 A1 | 6/2017 | Sharonov et al. |
| 2017/0216891 A1 | 8/2017 | Campanella et al. |
| 2017/0216892 A1 | 8/2017 | Campanella et al. |
| 2017/0216893 A1 | 8/2017 | Campanella et al. |
| 2017/0218730 A1 | 8/2017 | Campanella et al. |
| 2017/0218731 A1 | 8/2017 | Campanella et al. |
| 2017/0218732 A1 | 8/2017 | Campanella et al. |
| 2017/0254196 A1 | 9/2017 | Campanella et al. |
| 2017/0254787 A1 | 9/2017 | Campanella et al. |
| 2017/0328750 A1 | 11/2017 | Jehle et al. |
| 2018/0003572 A1 | 1/2018 | Garsd et al. |
| 2018/0003684 A1 | 1/2018 | Kerr |
| 2018/0024202 A1 | 1/2018 | Erickson et al. |
| 2018/0154408 A1 | 6/2018 | Ko et al. |
| 2018/0164137 A1 | 6/2018 | Layher et al. |
| 2018/0171604 A1 | 6/2018 | Kim et al. |

(56) References Cited

U.S. PATENT DOCUMENTS

| | | |
|---|---|---|
| 2018/0209248 A1 | 7/2018 | Patel et al. |
| 2018/0304323 A1 | 10/2018 | Campanella et al. |
| 2019/0069245 A1 | 2/2019 | Miller et al. |
| 2019/0232346 A1 | 8/2019 | Speer et al. |
| 2019/0277119 A1 | 9/2019 | Campion |
| 2019/0277821 A1 | 9/2019 | Quigley et al. |
| 2020/0086365 A1 | 3/2020 | Campanella et al. |
| 2020/0101504 A1 | 4/2020 | Quigley et al. |
| 2020/0101505 A1 | 4/2020 | Quigley et al. |
| 2020/0130033 A1 | 4/2020 | Campanella et al. |
| 2020/0197990 A1 | 6/2020 | Quigley et al. |
| 2020/0254497 A1 | 8/2020 | Campanella et al. |
| 2020/0306806 A1 | 10/2020 | Quigley et al. |
| 2020/0306807 A1 | 10/2020 | Quigley et al. |
| 2021/0046524 A1 | 2/2021 | Quigley et al. |
| 2021/0178436 A1 | 6/2021 | Quigley et al. |
| 2021/0229142 A1 | 7/2021 | Quigley et al. |
| 2021/0372977 A1 | 12/2021 | Campanella et al. |
| 2022/0008970 A1 | 1/2022 | Quigley et al. |
| 2022/0008971 A1 | 1/2022 | Quigley et al. |
| 2022/0008972 A1 | 1/2022 | Quigley et al. |
| 2022/0008973 A1 | 1/2022 | Quigley et al. |
| 2022/0062959 A1 | 3/2022 | Campanella et al. |
| 2022/0062960 A1 | 3/2022 | Campanella et al. |

FOREIGN PATENT DOCUMENTS

| | | | |
|---|---|---|---|
| WO | WO 2015/072989 A1 | 5/2015 | |
| WO | WO 2016/010985 A1 | 1/2016 | |
| WO | WO 2018/194650 A1 | 10/2018 | |
| WO | WO 2020/072457 A1 | 4/2020 | |

OTHER PUBLICATIONS

U.S. Appl. No. 15/456,936, Campanella et al., filed Mar. 13, 2017.
U.S. Appl. No. 15/456,982, Campanella et al., filed Mar. 13, 2017.
U.S. Appl. No. 15/464,236, Campanella et al., filed Mar. 20, 2017.
U.S. Appl. No. 15/478,583, Campanella et al., filed Apr. 4, 2017.
U.S. Appl. No. 15/493,174, Campanella et al., filed Apr. 21, 2017.
U.S. Appl. No. 15/493,184, Campanella et al., filed Apr. 21, 2017.
U.S. Appl. No. 15/493,201, Campanella et al., filed Apr. 21, 2017.
U.S. Appl. No. 16/024,085, Campanella et al., filed Jun. 29, 2018.
U.S. Appl. No. 16/290,387, Quigley et al., filed Mar. 2, 2019.
U.S. Appl. No. 16/589,372, Quigley et al., filed Oct. 1, 2019.
U.S. Appl. No. 16/589,391, Quigley et al., filed Oct. 1, 2019.
U.S. Appl. No. 16/694,745, Campanella et al., filed Nov. 25, 2019.
U.S. Appl. No. 16/726,232, Campanella et al., filed Dec. 23, 2019.
U.S. Appl. No. 16/745,892, Campanella et al., filed Jan. 17, 2020.
U.S. Appl. No. 16/831,131, Campanella et al., filed Mar. 26, 2020.
U.S. Appl. No. 16/901,405, Quigley et al., filed Jun. 15, 2020.
U.S. Appl. No. 16/901,430, Quigley et al., filed Jun. 15, 2020.
U.S. Appl. No. 16/927,471, Quigley et al., filed Jul. 13, 2020.
U.S. Appl. No. 16/927,479, Quigley et al., filed Jul. 13, 2020.
U.S. Appl. No. 16/927,482, Quigley et al., filed Jul. 13, 2020.
U.S. Appl. No. 16/927,488, Quigley et al., filed Jul. 13, 2020.
U.S. Appl. No. 17/086,987, Quigley et al., filed Nov. 2, 2020.
U.S. Appl. No. 17/152,252, Quigley et al., filed Jan. 19, 2021.
U.S. Appl. No. 17/167,539, Quigley et al., filed Feb. 4, 2021.
U.S. Appl. No. 17/343,317, Campanella et al., filed Jun. 9, 2021.
U.S. Appl. No. 17/369,395, Campanella et al., filed Jul. 7, 2021.
U.S. Appl. No. 17/369,318, Campanella et al., filed Jul. 7, 2021.
U.S. Appl. No. 17/959,446, Quigley et al., filed Oct. 4, 2022.
U.S. Appl. No. 18/168,983, Campanella et al., filed Feb. 14, 2023.
International Search Report and Written Opinion for International Application No. PCT/US2017/020196 dated Jun. 7, 2017.
Invitation to Pay Additional Fees for International Application No. PCT/US17/28818 dated Jul. 10, 2017.
International Search Report and Written Opinion for International Application No. PCT/US17/28818 dated Sep. 8, 2017.
International Search Report and Written Opinion for International Application No. PCT/US2019/020251 dated May 31, 2019.
Extended European Search Report for European Application No. 17760717.3 dated Oct. 2, 2019.
International Search Report and Written Opinion for International Application No. PCT/US2019/054013 dated Dec. 4, 2019.
Extended European Search Report for European Application No. 17906368.0 dated Oct. 15, 2020.
International Preliminary Report on Patentability for International Application No. PCT/US2019/054013 dated Apr. 15, 2021.
International Search Report and Written Opinion for International Application No. PCT/US2021/013850 dated Jun. 21, 2021.
International Search Report and Written Opinion for International Application No. PCT/US2021/040653 dated Nov. 26, 2021.
Communication pursuant to Article 94(3) EPC for European Application No. 17760717.3 dated Feb. 21, 2022.
Extended European Search Report for European Application No. 19869105.7 dated May 23, 2022.
Communication pursuant to Article 94(3) EPC for European Application No. 17906368.0 dated Aug. 4, 2022.
International Preliminary Report on Patentability for International Application No. PCT/US2021/013850 dated Aug. 11, 2022.
International Preliminary Report on Patentability for International Application No. PCT/US2021/040653 dated Jan. 26, 2023.
[No Author Listed], 50% CH4, 35% CO2, 15% N2. Instrument Depot. 2015. http://www.instrumentdepot.com/50-methane-35-carbon-dioxide-15-nitrogen-c-1_27_472.html [last accessed Sep. 25, 2015].
[No Author Listed], Cloud-Based Wellwatcher Analytics Platform Offers 24/7/365 Visibility on Landfill Gas-Collection Systems. Tech Note. Loci Controls. Nov. 2016. 1 page.
[No Author Listed], Increase Landfill Gas Collection By Up To 30%. Tech Note. Loci Controls. Oct. 2016. 1 page.
[No Author Listed], Loci Controller Combines Active Flow Control With 24/7/365 Real-Time Gas-Composition Analysis to Maximize Landfill Gas Extraction. Tech Note. Loci Controls. Nov. 2016. 1 page.
[No Author Listed], Loci Sentry Utilizes Passive Flow and Gas-Composition Monitoring in Conjunction With Loci Controller and Wellwatcher Analytics to Maximize Landfill Gas Collection. Tech Note. Loci Controls. Nov. 2016. 1 page.
[No Author Listed], Methacontrol® Optimizing landfill gas recovery. Oct. 9, 2013. http://www.veolia.com/en/veolia-group/media/news/methacontrol-r. 1 page.
Bieker et al., Real-Time Production Optimization of Offshore Oil and Gas Production Systems: A Technology Survey. SPE International. 2006. 8 pages.
Collins et al., Web-based monitoring of year-length deployments of autonomous gas sensing platforms on landfill sites. 2011 IEEE Sensors Proceedings. 2011:1620-3.
Fay et al., Remote Real-Time Monitoring of Subsurface Landfill Gas Migration. Sensors. 2011;11(7):6603-29.
Xu et al., Impact of changes in barometric pressure on landfill methane emission. AGU Publications. Jul. 10, 2014. 17 pages.

* cited by examiner

DEVICES AND TECHNIQUES RELATING TO LANDFILL GAS EXTRACTION

CROSS-REFERENCE TO RELATED APPLICATIONS

This application is a continuation of and claims priority under 35 U.S.C. § 120 to U.S. patent application Ser. No. 17/369,395, titled "Devices and Techniques Relating to Landfill Gas Extraction," filed Jul. 7, 2021, which is a continuation of and claims priority under 35 U.S.C. § 120 to U.S. patent application Ser. No. 16/831,131 (U.S. Pat. No. 11,084,074, issued Aug. 10, 2021), titled "Devices and Techniques Relating to Landfill Gas Extraction," filed Mar. 26, 2020 which is a continuation of and claims priority under 35 U.S.C. § 120 to U.S. patent application Ser. No. 15/456,936 (U.S. Pat. No. 10,639,687, issued on May 5, 2020), titled "Devices and Techniques Relating to Landfill Gas Extraction," filed Mar. 13, 2017, which is a continuation of and claims priority under 35 U.S.C. § 120 to U.S. patent application Ser. No. 14/532,807 (U.S. Pat. No. 10,029,290, issued Jul. 24, 2018), titled "Devices and Techniques Relating to Landfill Gas Extraction," filed Nov. 4, 2014, which claims the benefit under 35 U.S.C. § 119(e) of U.S. Provisional Application Ser. No. 61/899,828, titled "In-Situ Control Mechanisms for Landfill Gas Extraction Wells" and filed on Nov. 4, 2013, and U.S. Provisional Application Ser. No. 61/913,628, titled "System and Methods for Optimizing Landfill Gas Extraction" and filed on Dec. 9, 2013, each of which are hereby incorporated by reference herein in their entireties.

BACKGROUND

Technical Field

The devices and techniques described herein relate to controlling extraction of gas from landfills.

Discussion of the Related Art

Landfills typically produce landfill gas as a result of decomposition processes occurring in the waste, and methane is often a component of this landfill gas. In order to reduce emissions of methane and other contaminants in landfill gas, the landfill sites are typically capped with a layer of cover material and gas extraction systems are installed to pull landfill gas out before it can penetrate the cover layer and escape. At larger sites, these gas extraction systems can consist of a plurality of vertical and horizontal wells drilled into the landfill, which are connected with piping to one or more vacuum sources. The cover layer prevents gas from freely escaping, while the vacuum in the extraction wells pulls landfill gas into the collection system. A conventional landfill gas extraction well typically has a manual valve that adjusts the localized vacuum pressure in that well, as well as a set of ports for sampling the gas characteristics with a portable gas analyzer. Landfill gas is most often disposed of in a flare, processed for direct use, or used to power electricity generation equipment (such as generators or gas turbines).

SUMMARY

According to an aspect of the present disclosure, a method for controlling extraction of landfill gas from a landfill through a gas extraction system is provided, the method comprising: measuring a plurality of values indicating conditions associated with the landfill; with at least one computing device, computing, based at least in part on the plurality of values and on a model of the landfill, a predicted future state of the landfill; determining, based at least in part on the predicted future state of the landfill, one or more control parameters for one or more respective control devices configured to control operation of the gas extraction system; applying the one or more control parameters to the one or more respective control devices of the gas extraction system; and with the one or more control devices, controlling extraction of the landfill gas from the landfill based, at least in part, on the one or more respective control parameters.

According to another aspect of the present disclosure, an apparatus for controlling extraction of landfill gas from a landfill through a gas extraction system is provided, the apparatus comprising: one or more processors; and at least one computer-readable storage medium storing instructions which, when executed by the one or more processors, cause the apparatus to perform a method. The method includes controlling a plurality of sensors to measure a plurality of values indicating conditions associated with the landfill; predicting, based at least in part on the plurality of values and on a model of the landfill, a future state of the landfill; determining, based at least in part on the predicted future state of the landfill, one or more control parameters for one or more respective control devices of the gas extraction system; controlling application of the one or more control parameters to the one or more respective control devices of the gas extraction system; and controlling the one or more control devices to control extraction of the landfill gas from the landfill based, at least in part, on the one or more respective control parameters.

According to another aspect of the present disclosure, a gas extraction system for controlling extraction of landfill gas from a landfill is provided, the system comprising: at least one vacuum source; one or more control devices disposed in well piping and configured to control flow rates of the landfill gas through the well piping; one or more wells coupled to the at least one vacuum source through the well piping and through the one or more control devices disposed in the well piping; and one or more processors. The one or more processors are configured to measure a plurality of values indicating conditions associated with the landfill; predict, based at least in part on the plurality of values and on a model of the landfill, a future state of the landfill; determine, based at least in part on the predicted future state of the landfill, one or more control parameters for the one or more respective control devices; and apply the one or more control parameters to the one or more respective control devices, wherein the one or more control devices are configured to control extraction of the landfill gas from the landfill based, at least in part, on the one or more respective control parameters.

BRIEF DESCRIPTION OF THE DRAWINGS

Various aspects and embodiments will be described with reference to the following figures. It should be appreciated that the figures are not necessarily drawn to scale. For purposes of clarity, not every component may be labeled in every drawing. In the drawings.

DETAILED DESCRIPTION

Conventional techniques for controlling extraction of landfill gas are sometimes imprecise and inefficient. When such techniques are used, the gas extracted from a landfill may not have the desired properties (e.g., the energy content of the extracted gas may be lower than a desired energy content, the composition of the extracted gas may differ from a desired composition, etc.). In some cases, conventional techniques may even be counter-productive (e.g., such techniques may destroy some or all of the bacteria that convert decomposing waste into methane, thereby reducing the energy content of the landfill gas, or may result in emission of high levels of methane into the atmosphere).

The inventors have recognized and appreciated that controlling extraction of landfill gas based on a predictive model of the landfill may overcome at least some of the deficiencies of conventional landfill gas extraction techniques. For example, controlling extraction of landfill gas based on a predictive model of the landfill may increase precision and/or efficiency of the gas extraction process, thereby facilitating extraction of landfill gas having desired properties. As another example, controlling extraction of landfill gas based on a predictive model of the landfill may reduce the landfill's environmental impact (e.g., by reducing the amount of harmful and/or foul-smelling gas emitted into the atmosphere). In some embodiments, the performance of the gas extraction system may be enhanced by adjusting the system's control settings in real time or at frequent intervals (e.g., hourly or daily). In some embodiments, the performance of the gas extraction system may be enhanced by training the predictive model based on differences between the landfill state predicted by the model and the landfill state actually observed. In some embodiments, the performance of the gas extraction system may be enhanced by modeling interactions between/among two or more wells.

The aspects and embodiments described above, as well as additional aspects and embodiments, are described further below. These aspects and/or embodiments may be used individually, all together, or in any combination, as the application is not limited in this respect.

Figure 1:
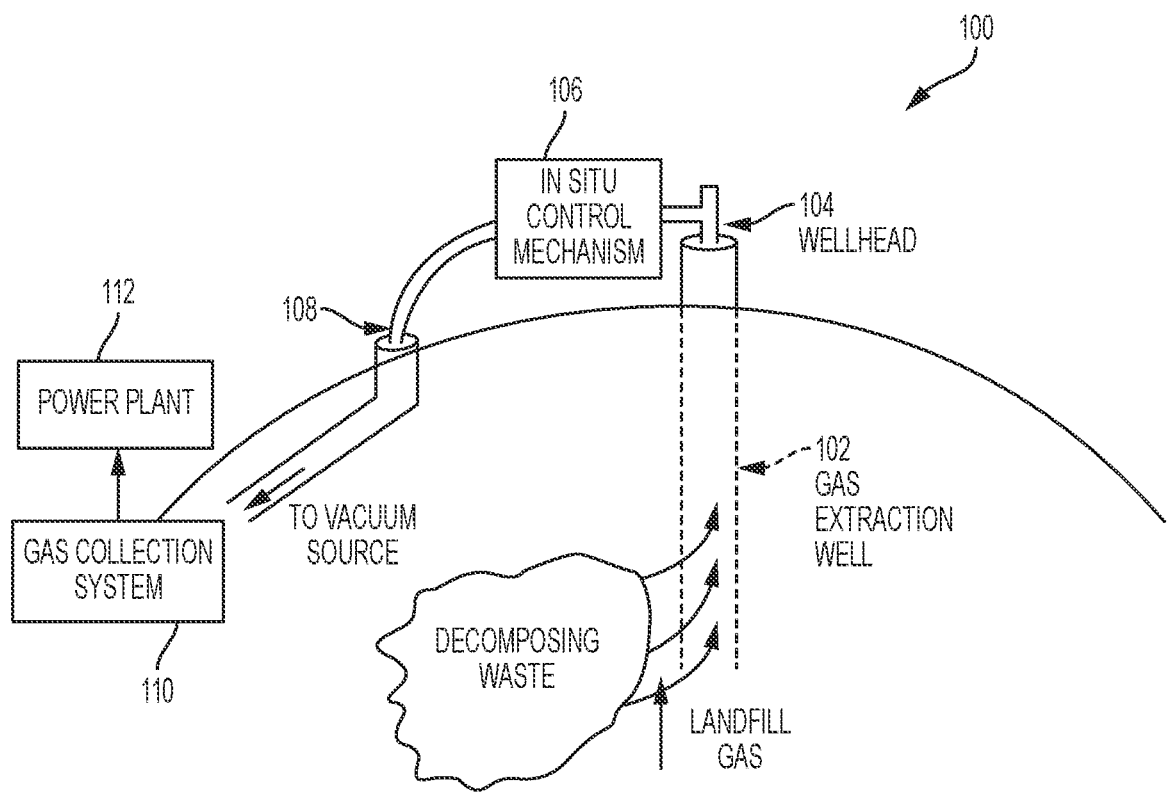
FIG. 1 is a sketch illustrating a landfill gas extraction system, according to some embodiments.
Figure 5:
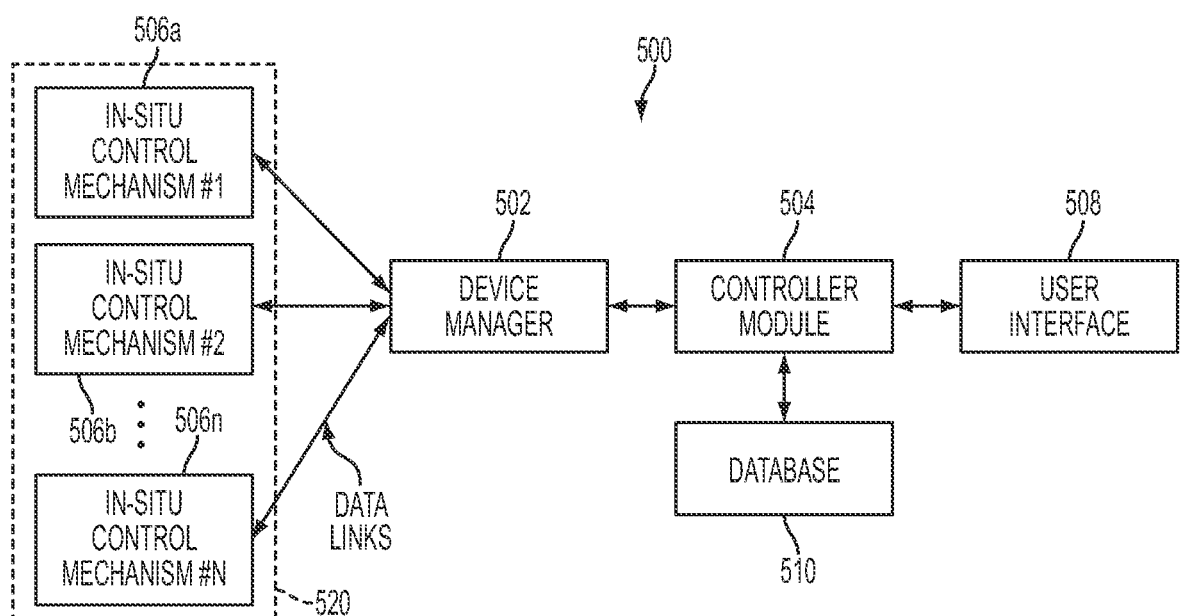
FIG. 5 is a block diagram illustrating an example of a control system for controlling landfill gas extraction, according to some embodiments.

This disclosure describes devices and techniques for controlling landfill gas extraction. FIG. 1 illustrates a landfill gas extraction system 100, according to some embodiments. In some embodiments, a landfill gas extraction system may include one or more gas extraction wells 102 coupled to one or more wellheads 104. In some embodiments, each wellhead may be in fluid communication with a single, corresponding well. In some embodiments, the landfill gas extraction system 100 may include a gas extraction piping system 108 coupling the well(s) 102 to a gas collection system 110, and one or more In Situ Control Mechanisms 106 for controlling extraction of the landfill gas through the well(s) 102 and gas extraction piping system 108 to the gas collection system 110. In some embodiments, gas collection system 110 may supply the extracted landfill gas to a gas-to-energy power plant 112, which may convert the landfill gas into electrical power (e.g., by burning the landfill gas to turn the rotor of a generator or turbine). In some embodiments, the In Situ Control Mechanism(s) 106 may operate (e.g., individually, in concert with each other, and/or under the control of a controller) to improve gas extraction efficiency and/or to control the extraction process for a variety of desired outcomes. In some embodiments the controller may be located remote from the In Situ Control Mechanisms. (Such a remotely located controller is not shown in FIG. 1, but is shown in FIG. 5 and discussed below.)

It should be appreciated that an In Situ Control Mechanism, as described herein, may control one or more parameters associated with a well, but is not a requirement that all other In Situ Control Mechanisms be physically located at that well. The In Situ Control Mechanism(s) may be disposed at any suitable location(s). In some embodiments, each In Situ Control Mechanism may be coupled to a single, corresponding well. In some embodiments, an In Situ Control Mechanism may be coupled to one or more wells. In some embodiments, some or all of the gas extraction wells in a landfill gas extraction system may be outfitted with an In Situ Control Mechanism 106, as depicted in FIG. 1. In some embodiments, an In Situ Control Mechanism 106 may be positioned at or adjacent to one or more junction points in the gas extraction piping system 108 (header junctions, or leachate junctions, or others) to control the performance of an entire section of piping. In some embodiments, an In Situ Control Mechanism 106 may be positioned between the gas extraction well 102 and the gas collection system 110 such that gas coming from the well flows through the In Situ Control Mechanism 106 on its way to the rest of the collection system. The In Situ Control Mechanism 106 may be installed permanently in a suitable location (e.g., in, on, adjacent to, and/or near a well and/or gas extraction piping), or may be moved from location to location (e.g., well to well) over time.

Figure 2:
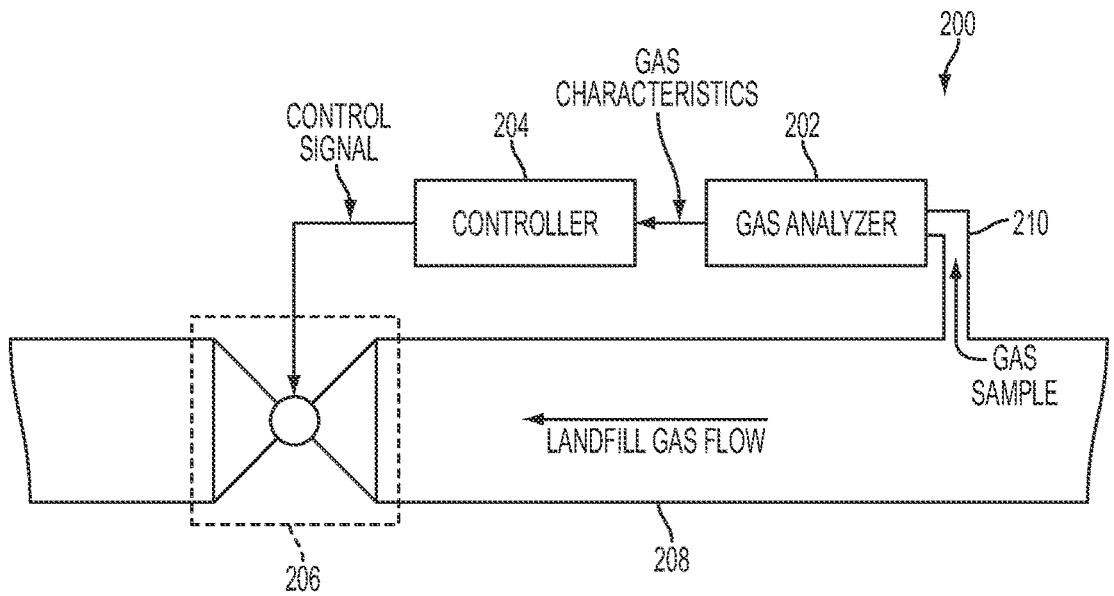
FIG. 2 is a block diagram illustrating an in situ control mechanism for landfill gas extraction, according to some embodiments.

A block diagram of some embodiments of an In Situ Control Mechanism 200 is presented in FIG. 2. In some embodiments, an In Situ Control Mechanism may include one or more mechanisms configured to control the flow of landfill gas from one or more wells to gas collection system 110 through gas extraction piping system 108. Any suitable flow-control mechanism 206 may be used, including, without limitation, a valve (e.g., a solenoid valve, latching solenoid valve, pinch valve, ball valve, butterfly valve, ceramic disc valve, check valves, choke valves, diaphragm valves, gate valves, globe valves, knife valves, needle valves, pinch valve, piston valve, plug valve, poppet valve, spool valve, thermal expansion valve, pressure reducing valve, sampling valve, safety valve) and/or any other suitable type of flow-control mechanism.

In some embodiments, an In Situ Control Mechanism may include one or more actuation devices configured to control operation of the one or more flow-control mechanisms (e.g., to open a flow-control mechanism, close a flow-control mechanism, and/or adjust a setting of a flow-control mechanism). In some embodiments, an In Situ Control Mechanism may include a controller 204 configured to determine the settings to be applied to the one or more flow-control mechanisms (e.g., via the actuation devices), and/or configured to apply the settings to the one or more flow-control mechanisms (e.g., via the actuation devices). In some embodiments, the settings to be applied to the one or more flow-control mechanisms (e.g., via the actuation devices) may be determined remotely and communicated to the In Situ Control Mechanism (e.g., by a remotely located controller) using any suitable communication technique, including, without limitation, wireless communication, wired communication, and/or power line communication.

In some embodiments, an In Situ Control Mechanism may include one or more sensor devices configured to sense one or more attributes associated with the landfill, including, without limitation, attributes of the landfill, attributes of the landfill gas, attributes of an area adjacent to the landfill, and/or attributes of the landfill's gas extraction system. In some embodiments, the In Situ Control Mechanism may include one or more actuation devices configured to control operation of the one or more sensor devices (e.g., to activate a sensor device, deactivate a sensor device, and/or collect data from the sensor device). In some embodiments, an In Situ Control Mechanism may include a controller 204 configured to determine the settings (e.g., control signals) to be applied to the one or more actuation and/or sensor devices, configured to apply the settings to the one or more actuation and/or sensor devices, and/or configured to collect data (e.g., measurements) obtained by the one or more sensor devices. In some embodiments, the settings to be applied to the one or more actuation and/or sensor devices may be determined remotely and communicated to the In Situ Control Mechanism (e.g., by a remotely located controller) using any suitable communication technique, including, without limitation, wireless communication, wired communication, and/or power line communication. In some embodiments, the In Situ Control Mechanism may communicate the one or more sensed attributes associated with the landfill (e.g., to a remotely located controller).

In some embodiments, the one or more sensor devices may include a Gas Analyzer 202. In some embodiments, a Gas Analyzer 202 may collect a sample of landfill gas from the gas extraction piping 208 through an input port 210, determine (e.g., compute, measure and/or sense) one or more characteristics of that gas, and/or report the one or more characteristics of the gas to a controller (e.g., local controller 204 and/or a remotely located controller). In some embodiments, the Gas Analyzer may determine the gas temperature, pressure, flow rate, humidity, density, gas composition (partial pressure or concentration of methane, oxygen, carbon dioxide, carbon monoxide, hydrogen sulfide, and/or any other suitable gas) and/or any other characteristics of the landfill gas coming from the gas extraction well(s) upstream from the location where the In Situ Control Mechanism is installed. The gas characteristics may be sampled once in each reading, or may be sampled many times and statistics about the distribution of values may be determined. The gas characteristics may be continuously determined, or they may be determined at discrete time intervals. In some embodiments, the Gas Analyzer may analyze gas in the main flow of landfill gas (e.g., within gas extraction piping 208). In some embodiments, the Gas Analyzer may draw a small sample of gas into a separate chamber for analysis. In some embodiments, certain parameters (for example flow rate, pressure, temperature, humidity, and the like) may be measured in the main gas stream (e.g., may be measured by sensors disposed directly within extraction gas piping), and others may be analyzed in a separate chamber.

In order to improve measurement accuracy, measurement resolution, measurement repeatability, sensor lifetime, and/or sensor reliability, a sample of gas from the well may be pre-treated before analysis, which pre-treatment may include heating, cooling, drying, and/or any other suitable pre-treatment processing (e.g., through forced condensation, passing through a desiccant, or any other suitable technique), filtered to remove particles, filtered to remove contaminants or other chemicals, pressurized, de-pressurized, and/or otherwise treated before being analyzed. After analyzing and reporting gas characteristics (e.g., to local controller 204 and/or to a remotely located controller), the Gas Analyzer may purge the gas sample from the chamber and vent it to the atmosphere, or return it to the main gas flow. In some embodiments, the analyzed gas sample may be purged prior to reporting the gas characteristics to a controller.

One embodiment of a Gas Analyzer 300 utilizing pre-treatment mechanisms as described above is illustrated in FIG. 3. In the Gas Analyzer 300 of FIG. 3 and other arrangements not explicitly described here, a small sample of landfill gas may be taken into the Gas Analyzer through input port 310 (e.g., from the main flow of landfill gas in gas extraction piping 308 between the gas extraction well and the gas collection system) and sent through a drying element 312 and a series of one or more flow-control mechanisms (e.g., valves) before entering the gas analysis sample chamber 302. In some embodiments, at the beginning and end of a gas measurement cycle, both valves 316 and 318 are in the closed state. Valve 316 may be opened and the pump 314 may be turned on in order to draw a sample of landfill gas through the drying element 312 and into the gas analysis sample chamber 302 for analysis. At the end of a measurement cycle, the pump 314 may be turned off and valve 316 may be closed to stop the flow of gas into the sample chamber 302. In some embodiments, the gas sample may be purged from sample chamber 302 by opening valve 318. Under typical operating conditions, the gas collection system and gas extraction well(s) may be at negative pressure (i.e., operating under vacuum conditions) relative to atmospheric pressure, such that opening valve 318 may pull ambient air through the Gas Analyzer 300 to purge the sample chamber 302 of landfill gas. In some embodiments, one or more valves of Gas Analyzer 300 may be toggled and a pump (e.g., pump 314) may be activated to force purge sample chamber 302 with ambient air. Forced purging may be beneficial when one or more wells upstream from Gas Analyzer 300 are operating under positive pressure relative to atmospheric pressure (e.g., because the gas extraction system's vacuum is off-line or because the one or more wells are under-extracted). For example, forced purging may be an effective technique for clearing condensate from the Gas Analyzer's tubes and/or for clearing sample gas from sample chamber 302 in cases where the upstream well(s) are operating under positive pressure. (Although not shown, one of ordinary skill in the art would understand that a valve may be placed between pump 314 and input port 310, and that sample chamber 302 may be force purged by closing this valve and by opening valves between pump 314 and atmospheric port 320.) After purging the gas sample from Gas Analyzer 300, valve 318 may be closed to stop atmospheric air from leaking into the gas collection system.

Figure 3:
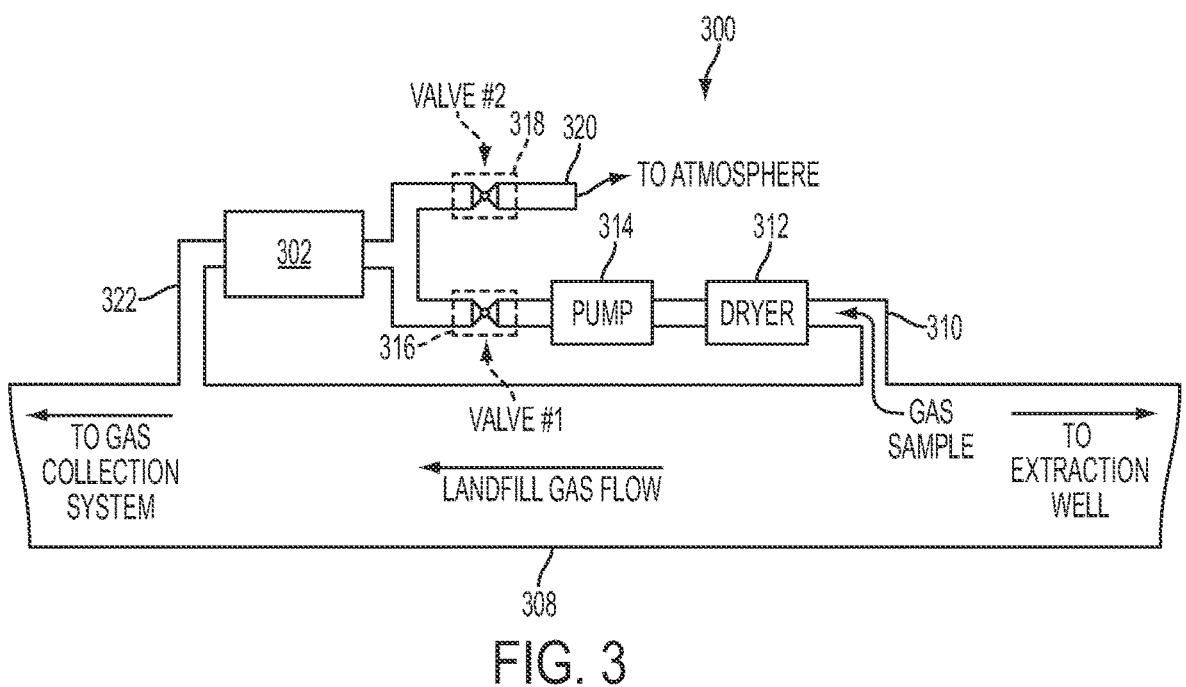
FIG. 3 is a block diagram illustrating a gas analyzer of an in situ control mechanism for landfill gas extraction, according to some embodiments.

Configurations that perform a similar function to the embodiment of FIG. 3 and which, while not described explicitly here, are within the scope of the present disclosure. For example, the pump 314 may be placed after valve 316, or after the gas analyzer sample chamber 302, or the drying element 312 may be moved to a different point in the flow path. Similarly, the functionality provided by valve 316 and the pump 315 may be consolidated by the use of a sealed pump design (e.g., a peristaltic pump). An additional valve may be added after the gas analyzer (e.g., in a port 322 coupling the sample chamber 302 to the gas extraction piping 308), for additional control or to prevent backflow into the sample chamber. Additionally, the Gas Analyzer may be outfitted with additional modules to provide other pre-treatment of the gas in addition to or in alternative to drying (for example, particle filtering, removal or deactivation of hydrogen sulfide or other chemicals, etc.).

In some embodiments, the flow-control mechanism(s) of Gas Analyzer 300 may include solenoid valves, latching solenoid valves, pinch valves, ball valves, butterfly valves, ceramic disc valves, check valves, choke valves, diaphragm valves, gate valves, globe valves, knife valves, needle valves, pinch valves, piston valves, plug valves, poppet valves, spool valves, thermal expansion valves, pressure reducing valves, sampling valves, safety valves, and/or any other type of flow-control mechanism.

In some embodiments, the Gas Analyzer may utilize non-dispersive infrared (NDIR) sensors, catalytic beads, electrochemical sensors, pellistors, photoionization detectors, zirconium oxide sensors, thermal conductivity detectors, and/or any other sensing technology. Flow rate may be measured by a pressure differential across a venturi, orifice plate, or other restriction to the flow of gas; by pitot tube, mechanical flow meter, heated wire or thermal mass flow meter, and/or using any other suitable technique. Temperature may be measured with a thermocouple, a negative or positive temperature coefficient resistor, capacitor, inductor, a semiconducting device, and/or using any other suitable technique. Temperature may be measured inside the well, in the main gas flow from the well to the collection system, inside a sampling chamber, outside of the control mechanism (e.g., ambient atmospheric temperature), and/or at any other suitable point. Temperature, pressure, gas composition, and/or other readings from different points within the gas extraction well, the In Situ Control Mechanism, and/or the gas collection system may be used in conjunction with each other to obtain a more complete analysis of the operating state of the landfill gas collection system.

Figure 4:
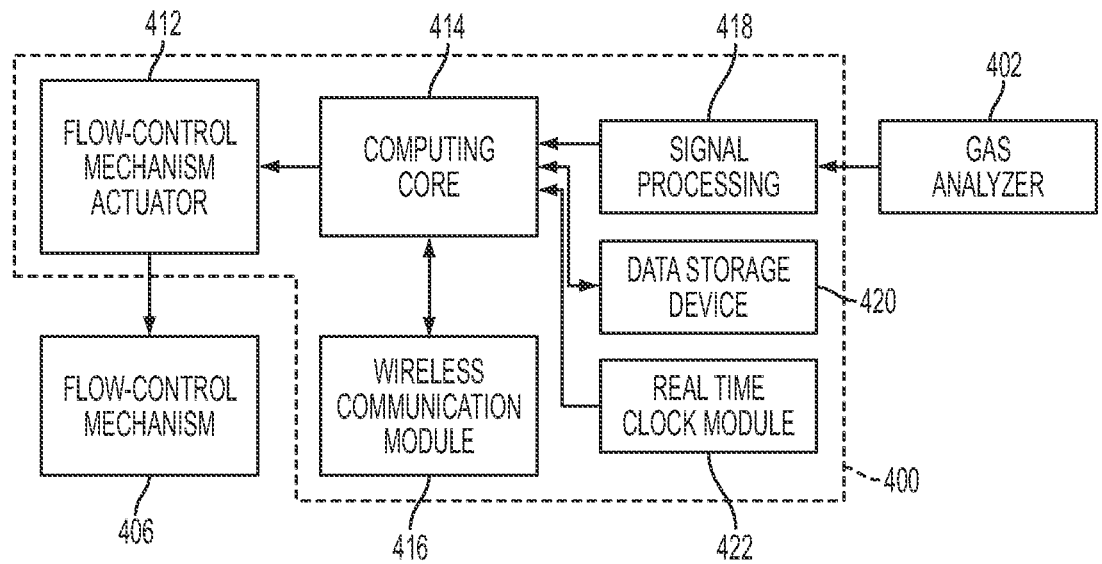
FIG. 4 is a block diagram illustrating a controller of an in situ control mechanism for landfill gas extraction, according to some embodiments.

FIG. 4 shows a controller of an In Situ Control Mechanism, according to some embodiments. In some embodiments, the Controller 400 of an In Situ Control Mechanism may include functional blocks as indicated in FIG. 4. In the embodiment of FIG. 4, the Controller 400 includes a Signal Processing Module 418, a Data Storage Device 420, a Real Time Clock Module 422, a Wireless Communication Module 416, and/or a Flow-Control Mechanism Actuator 412 (e.g., valve drive buffer) for providing a control signal to the Flow-Control Mechanism 406. Other embodiments may use only parts of this implementation, while others may add additional functional modules for supporting functions. For example, in some embodiments, the Controller of an In Situ Control Mechanism may be implemented using a one or more processors as described below.

In some embodiments, the Controller 400 of the In Situ Control Mechanism may use data about environmental conditions in and around the landfill (e.g., in and around the gas extraction well upon which the In Situ Control Mechanism is installed) to determine the settings to be applied to the flow-control mechanism. In some embodiments, a remotely-located controller may use the environmental data to determine the settings to be applied to the flow-control mechanism, and may communicate those settings to the In Situ Control Mechanism. The environmental data may include information about parameters including, but not limited to atmospheric pressure, ambient temperature, wind direction, wind speed, precipitation, and/or any other suitable environmental parameter. The In Situ Control Mechanism may use information from other sensors placed in or around the gas extraction well, including, without limitation, subsurface temperature probes, subsurface moisture probes, measurements of the chemical and/or biological processes (for example, pH measurements, tests for the presence of other chemicals or biological by-products, etc.) occurring in the section of waste that is in the vicinity of the gas extraction well, and/or any other suitable information.

In some embodiments, the Controller 400 of the In Situ Control Mechanism may use the current data about the gas characteristics and/or environmental parameters, and/or it may incorporate historical data about the performance of the gas extraction well to determine the settings to be applied to the Flow-Control Mechanism. In some embodiments, a remotely-located controller may use the gas data, environmental data, and/or historical data to determine the settings to be applied to the flow-control mechanism, and may communicate those settings to the In Situ Control Mechanism. The In Situ Control Mechanism may, in some embodiments, incorporate past and/or present data about gas production into one or more predictive models and may use the predictive model(s) to determine the modulation of the Flow-Control Mechanism state.

In some embodiments, the Signal Processing Module 418 takes gas characteristics data from the Gas Analyzer 402 and converts it into a form that can be interpreted by the Computing Core 414. This may involve a interpreting a serial digital data stream via a serial parsing algorithm, a parallel parsing algorithm, analog signal processing (for example, performing functions on analog signals like filtering, adding or removing gain, frequency shifting, adding or removing offsets, mixing or modulating, and the like), digital signal processing (digital filtering, convolution, frequency shifting, mixing, modulating, and the like), analog-to-digital or digital-to analog conversion, and/or any other suitable signal processing technique that will be recognized by one of ordinary skill in the art.

In some embodiments, the Data Storage Device 420 may include any volatile and/or non-volatile memory element, including but not limited to flash memory, SD card, micro SD card, USB drive, SRAM, DRAM, RDRAM, disk drive, cassette drive, floppy disk, cloud storage backup, and/or any other suitable computer-readable storage medium. The Data Storage Device may serve as a data recovery backup, or it may hold data for temporary intervals during the calculation of control signals. The Data Storage Device may be removable, or it may be fixed.

In some embodiments, the Real Time Clock Module 422 may include any circuit and/or functional module that allows the Computing Core to associate the results of a gas analyzer reading with a date or time (e.g., a unique date or time stamp).

In some embodiments, the Wireless Communication Module 416 may include, but is not limited to: a radio transceiver (AM or FM, or any other type), television, UHF, or VHF transceiver, Wi-Fi and/or other 2.4 GHz communication module, cellular chipset (2G, 3G, 4G, LTE, GSM, CDMA, etc.), GPS transmitter, satellite communication system, and/or any other suitable wireless communication device. The Wireless Communication Module may have an integrated antenna, and/or an external one. The Wireless Communication Module may transmit, receive, and/or have two-way communication with a central source and/or be capable of point-to-point communication with another module. In some embodiments, the Wireless Communication Module may include a 2G chipset that allows the In Situ Control Mechanism to connect to existing telecommunications infrastructure.

In some embodiments, the Computing Core 414 may include, but is not limited to: a microprocessor, a computer, a microcontroller, a field programmable gate array (FPGA), an application specific integrated circuit (ASIC), a digital signal processor (DSP), an analog computer or control system, and/or any other suitable computing device. In some embodiments, the Computing Core may have integrated Analog-to-Digital converters, pulse width modulation detectors, edge detectors, frequency detectors, phase detectors, amplitude detectors, demodulators, RMS-DC converters, rectifiers, and/or other suitable signal processing modules.

In some embodiments, the Flow-Control Mechanism Actuator 412 (e.g., a valve drive buffer) may include any circuit that can translate commands from the Computing Core into an appropriate actuation signal (e.g., driving signal) for the Flow-Control Mechanism 406. In some embodiments, translating commands from the Computing Core may comprise analog signal processing on a voltage (for example, adding/removing gain, offset, filtering, mixing, etc.), analog signal processing on a current control (for example, conversion to a 4-20 mA control loop, increasing output current drive capability), pulse width modulating a digital signal, digital signal processing, digital-to-analog or analog-to-digital conversion, and/or any other suitable techniques.

In some embodiments, the Flow-Control Mechanism 406 of the In Situ Control Mechanism may comprise a solenoid valve, latching solenoid valve, pinch valve, ball valve, butterfly valve, ceramic disc valve, check valve, choke valve, diaphragm valve, gate valve, globe valve, knife valve, needle valve, pinch valve, piston valve, plug valve, poppet valve, spool valve, thermal expansion valve, pressure reducing valve, sampling valve, safety valve, and/or any other suitable type of flow-control mechanism. The Flow-Control Mechanism may have two or more discrete operating states, or it may provide continuous adjustment of the operating state (e.g., valve position) for fine control of operating pressure, temperature, flow, gas characteristics, etc.

In some embodiments, the In-Situ Control Mechanism may modulate the Flow-Control Mechanism to achieve any number of desired outcomes, or it may determine the state of the Flow-Control Mechanism based on an optimization and/or prioritization of multiple output parameters. Some examples of control schemes might include, but are not limited to:

Modulation of the flow-control mechanism to maintain and/or obtain a constant vacuum pressure in the gas extraction well (in spite of varying atmospheric pressure, temperature, and/or varying rates of gas generation, etc.);

Modulation of the flow-control mechanism to maintain and/or obtain a constant flow rate of landfill gas from the extraction well;

Modulation of the flow-control mechanism to control the flow rate of landfill gas from the extraction well;

Modulation of the flow-control mechanism to maintain and/or obtain a constant percentage of any of the constituent gases (including but not limited to methane, carbon dioxide, oxygen, nitrogen, etc.) in the landfill gas coming from the extraction well;

Modulation of the flow-control mechanism to control (e.g., increase or decrease) the concentration of any of the constituent gases in the landfill gas coming from the extraction well;

Modulation of the flow-control mechanism to control (e.g., increase and/or decrease) the energy content of the landfill gas (e.g., increase the total quantity of methane extracted in a given period of time, etc.) coming from the extraction well;

Modulation of the flow-control mechanism to control the total volume of the landfill gas (e.g., increase the total quantity of landfill gas extracted in a given period of time, etc.) coming from the extraction well;

Modulation of the flow-control mechanism to increase the rate of extraction during periods of increased energy demand (e.g., increasing generation during the peaks of real time, hourly, daily, weekly, monthly, or seasonal electricity prices);

Modulation of the flow-control mechanism to decrease the rate of extraction during periods of reduced energy demand (e.g., reducing generation during the lows of real time, hourly, daily, weekly, monthly, or seasonal electricity prices);

Modulation of the flow-control mechanism to control (e.g., maintain, improve, and/or establish) the long term stability of the biochemical decomposition processes (aerobic or anaerobic digestion, etc.) occurring within the section of waste that is in the vicinity of the gas extraction well;

Modulation of the flow-control mechanism to control (e.g., increase and/or decrease) the rates of decomposition occurring within the section of waste that is in the vicinity of the gas extraction well;

Modulation of the flow-control mechanism to match the operating parameters or limitations of the gas collection system;

Modulation of the flow-control mechanism to prevent or extinguish underground fires or other potentially dangerous events occurring within the section of waste that is in the vicinity of the gas extraction well;

Modulation of the flow-control mechanism to mitigate emission of odors;

Modulation of the flow-control mechanism to control (e.g., reduce) emissions of landfill gas or components of landfill gas ($H_2S$, methane, etc.) in the vicinity of the gas extraction wells;

Modulation of the flow-control mechanism to control (e.g., reduce) gas losses into the atmosphere;

Modulation of the flow-control mechanism to control (e.g., maintain, improve, and/or establish) compliance of the gas extraction system with local, state and/or federal regulations; and/or Modulation of the flow-control mechanism to reduce damage to an engine, turbine, or other energy generation equipment from contaminants emanating from the vicinity of a gas extraction well.

In some embodiments, some or all of the gas extraction wells and/or piping junction points in a landfill may be outfitted with In-Situ Control Mechanisms to form at least a portion of a control system for controlling gas extraction across the entire landfill or a set of wells within the landfill (the "landfill under control"). One embodiment of such a control system is shown in FIG. 5.

FIG. 5 shows a control system 500 for a landfill gas extraction system, according to some embodiments. In some embodiments, control system 500 may include one or more In Situ Control Mechanisms 506 configured to control gas flow in a gas extraction system in a landfill under control 520. In some embodiments, control system 500 may include a controller module 504 for modeling aspects of the landfill under control, for communicating with the In Situ Control Mechanisms, and/or for controlling the operation of the In Situ Control mechanisms. In some embodiments, controller module 504 may be implemented on one or more computers located remotely from the In Situ Control Mechanisms (e.g., on a centralized computer or in a distributed computing environment). In some embodiments, controller module 504 may execute a multitasking program with different tasks configured to control the operation of different In Situ Control Mechanisms and/or to communicate with different In Situ Control Mechanisms. In some embodiments, the functionality described below as being performed by controller module 504 may be performed by one or more In Situ Control Mechanisms 506 individually or in concert. In some embodiments, controller module 504 may communicate with the In Situ Control Mechanisms through a device manager 502. In some embodiments, controller module 504 be in communication with a user interface 508 and/or a database 510.

In some embodiments, some or all of these In-Situ Control Mechanisms 506 may contain wireless communication capability to establish Wireless Data Links to controller module 504 (e.g., through device manager 502). Wireless Data Links may operate in either a unidirectional or a bidirectional manner. The network of Wireless Data Links may be implemented using a mesh network, a star network, point-to-point communication, and/or any other suitable communication technique. In-Situ Control Mechanisms 506 may send information over a communication network to a distributed network (e.g., the "cloud"). Communication may occur through a system including but not limited to a cell phone network (2G, 3G, 4G LTE, GSM, CDMA 1×RTT, etc.), a satellite network, a local area network connected to the Internet, etc. In some embodiments, the In Situ Control Mechanisms 506 may communicate with each other and/or with controller module 504 using wired data links, Wireless Data Links, power line communication, and/or any other suitable communication technique.

Information sent (e.g., over Wireless Data Links) by the In-Situ Control Mechanisms 506 may include but is not limited to sensor data, environmental data, failure notifications, status notifications, calibration notifications, etc. Information received by the In-Situ Control Mechanisms may include but is not limited to: raw or pre-processed data about the current or past operational state of other landfill gas extraction wells in the landfill under control, command and control signals, desired operating states, predictive calculations about the operating state of the well upon which the In-Situ Control Mechanism is installed or other landfill gas extraction wells, failure notifications, status notifications, calibration changes, software and/or firmware updates, flow-control mechanism settings, sensor settings, and/or other information.

In some embodiments, In Situ Control Mechanisms 506 in the landfill under control 520 may communicate with a Device Manager 502, as indicated in FIG. 5, and/or they may communicate directly with each other. The Device Manager 502 may include software operating on a computer in the landfill under control, or operating on a remote server, and/or operating on a distributed computing network ("the cloud") in one or multiple locations. In some embodiments, Device Manager 502 may be implemented using a computing system 1100 as described below. The Device Manager 502 may collect information from alternate sources—including but not limited to environmental data, past history about electrical power demand and/or prices, forecasts about future electrical power demand and/or prices, etc. In some embodiments, the Device Manager 502 may be in constant communication with the In-Situ Control Mechanisms 506, or it may communicate asynchronously with the In-Situ Control Mechanisms. In some embodiments, the Device Manager 502 may hold a queue of commands or other information to be passed to the In Situ Control Mechanism(s) 506 upon the establishment of a data link (e.g., re-establishment of a Wireless Data Link).

In some embodiments, the Device Manager 502 may associate a set of In-Situ Control Mechanisms 506 into a single landfill under control 520, and it may add or remove additional In-Situ Control Mechanisms 506 to that landfill under control 520 to accommodate the addition or removal of In-Situ Control Mechanisms from the site. The Device Manager 502 may contain or perform authentication or encryption procedures upon establishing a data link (e.g., a Wireless Data Link) with an In-Situ Control Mechanism. Security protocols implemented by the Device Manager may include, but are not limited to: internet key exchange, IPsec, Kerberos, point to point protocols, transport layer security (TLS), HTTPS, SSH, SHTP, etc.

In some embodiments, the Device Manager 502 may communicate with a controller module 504. The controller module 504 may include one or more applications running on a distributed computational platform (e.g., a "cloud server"), a traditional server infrastructure, a computing system 1100 as described below, and/or other suitable computer architecture recognized by those of ordinary skill in the art. It should be appreciated, however, that control functions as described herein may be distributed across device manager 502, controller module 504 and/or any other computing components in any suitable way. Similarly, control functions may be distributed across processors (e.g., controllers) associated with one or more In Situ Control Mechanisms.

In some embodiments, control system 500 may be configured to predict future states of the landfill under control, and/or may be configured to use such predictions to control the operation of a gas extraction system associated with the landfill under control. In some embodiments, using one or more predictions regarding the future state(s) of the landfill under control to control the operation of the gas extraction system may improve the performance (e.g., efficiency) of the gas extraction system, relative to the performance of conventional gas extraction systems.

Figure 6:
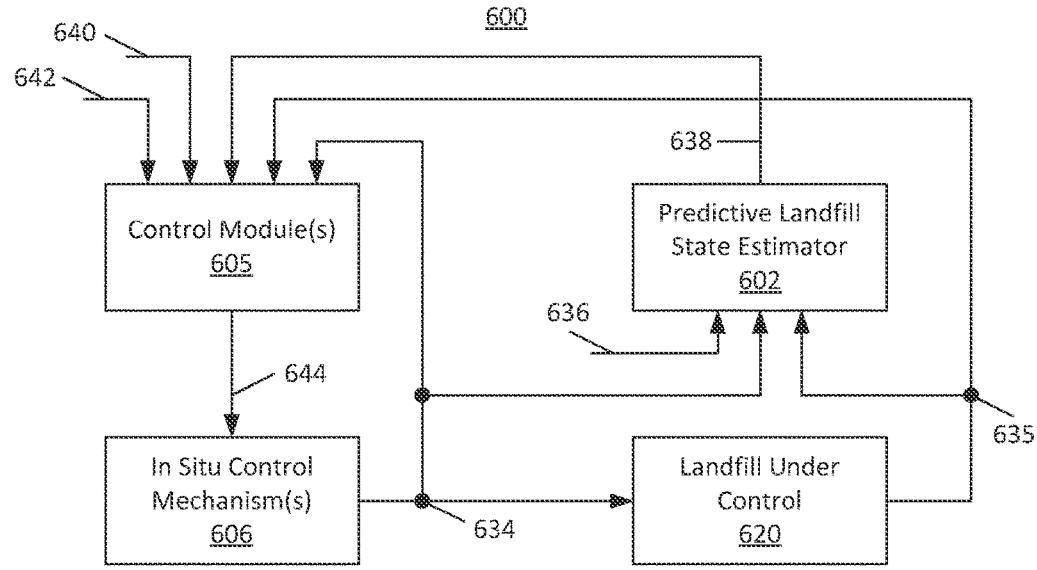
FIG. 6 is a block diagram illustrating an example of a feedback-based, predictive system for controlling landfill gas extraction, according to some embodiments.

FIG. 6 shows a feedback-based, predictive control system 600, which may be implemented by some embodiments of control system 500 to control the operation of gas extraction system associated with a landfill under control 620. Feedback-based, predictive control system 600 may include a predictive landfill state estimator 602 for predicting one or more future states of a landfill under control 620, and one or more control modules 605 for controlling the operation of a gas extraction system (e.g., by controlling the operation of one or more in situ control mechanisms 606 in the landfill under control 620) based, at least in part, on the predicted future state(s) of the landfill under control 620. The predictive landfill state estimator 602 and/or control module(s) 605 may be implemented by controller 504 and/or by controller(s) 204 of in situ control mechanism(s) 606, with the functions of the predictive landfill state estimator 602 and the control module(s) 605 being divided among the controller 504 and the in situ control mechanism(s) 606 in any suitable way.

In some embodiments, predictive landfill state estimator 602 may include one or more predictive models of the landfill under control 620. Each model may relate a set of parameters defining a current state of the landfill to one or more sets of parameters, defining one or more future states of the landfill. Any suitable modeling techniques may be used to develop such a model, which may be implemented using software programming on a computing device. Different models may be selected depending on parameters defining input or output states. For example, different models may be used to predict parameters such as odor, energy production, or gas production.

In some embodiments, predictive landfill state estimator 602 may use a predictive model to predict a future state 638 of at least one attribute of a landfill under control, based on a model of the landfill under control and/or based on suitable input data. In some embodiments, the predictive landfill state estimator 602 may apply mathematical models to present and/or past data about the landfill under control 620 (e.g., data about landfill gas production and/or extraction) to estimate a future state of the landfill under control (e.g., the future LFG production and/or extraction). Suitable input data for the predictive landfill state estimator 602 may include the current state 634 of flow-control mechanisms in the gas extraction system of the landfill under control (e.g., the operating states of valves in the gas extraction system), the current state 635 of the landfill under control (e.g., the characteristics of the landfill's gas, as determined using the in situ control mechanism's sensors), and/or environmental data 636 (e.g., data describing environmental conditions in and/or around the landfill, as determined by the in situ control mechanism's sensors or any other suitable data source). In some embodiments, the predicted future state may correspond to a specified date and/or time in the future.

In some embodiments, control module(s) 605 may control the operation of the gas extraction system based, at least in part, on the predicted future state 638 of the landfill under control. For example, control module(s) 605 may determine the values of control parameters 644 ("control settings") for the in situ control mechanism(s) 606 based on the predicted future state 638. In embodiments where the control module(s) are not implemented by the in situ control mechanism(s) 606, the control module(s) may send the determined values of the control parameters 644 to the in situ control mechanism(s) 606. The in situ control mechanism(s) 606 may apply the control parameters to flow-control mechanisms in the gas extraction system (e.g., valves) to control the operation of the gas extraction system (e.g., the in situ control mechanism(s) 606 may adjust the gas extraction rate from the landfill under control 620 by modulating the positions of valves in the gas extraction system). As another example, control module(s) 605 may determine changes in the current values of control parameters 644 for the in situ control mechanisms(s) 606 based on the predicted future state, and the in situ control mechanism(s) may change the control parameters of the flow-control mechanisms by the determined amounts.

In some embodiments, control module(s) 605 may determine the values (or changes in the values) of the control parameters 644 based on predicted future state 638 and/or based on other input data. For example, control module(s) 605 may determine a difference between a predicted and a desired future state, determine control parameters 644 to reduce that difference, and apply the control parameters to in situ control mechanism(s) 606 (e.g., by controlling an in situ control mechanism to adjust a valve or other actuator in accordance with the control parameters) to reduce that difference. The input data may include the current state 634 of flow-control mechanisms in the gas extraction system, the current state 635 of the landfill under control, design constraints 640, and/or set point(s) 642.

In some embodiments, design constraints 640 may include physical limitations of the landfill gas extraction system including, but not limited to: operating ranges of the flow-control mechanisms (e.g., available valve movement range), accuracy of the operating states of the flow-control mechanisms (e.g., valve position accuracy), resolution of the operating states of the flow-control mechanisms (e.g., valve position resolution), gas extraction system vacuum pressure, measurement ranges of the in situ control mechanism(s)' sensors, power generation capacity at a landfill gas to energy power plant, total flow rate restrictions of the landfill gas extraction system, and/or any other suitable limitations. In some embodiments, design constraints 640 may be hard-coded values, and/or they may be specific to particular well, collection of wells, landfills, or geographic regions. In some embodiments, design constraints may be re-programmed by a human operator through a software or hardware interface (for example, a web application, a mobile application, through manual or over the air firmware upgrades, etc.). Control module 605 may use these design constraints, for example, in selecting values of control parameters such that the design constraints are not violated.

In some embodiments, the set point(s) 642 may indicate a desired operating state for the gas extraction system (e.g., an energy content extraction rate, gas flow rate, gas composition, and/or other suitable characteristic for the gas extraction system, for individual wells, and/or for individual in situ control mechanisms). In some embodiments, the control module(s) 605 may determine the values of the control parameters 644 (e.g., using a mathematical model or models) to maintain the state of the landfill under control equal to, less than, or greater than the set point. In this manner, the control module(s) 605 may use the state of the landfill (e.g., the current and/or predicted states of the landfill) to control the gas extraction system to operate in a desired operating state (as indicated by the set point(s)), without violating the system's design constraints. The set point(s) may be hard coded into the system, may be user adjustable via a software interface (e.g., web or mobile application), and/or may be set and/or adjusted using any other suitable technique.

Predictive landfill state estimator 602 may obtain its input data using any suitable technique. In some embodiments, predictive landfill state estimator 602 may obtain the current state 634 of the flow-control mechanisms in the gas extraction system and/or the current state 635 of the landfill from the in situ control mechanism(s) 606 (e.g., by querying the in situ control mechanism(s) 606 via the Device Manager).

Figure 7:
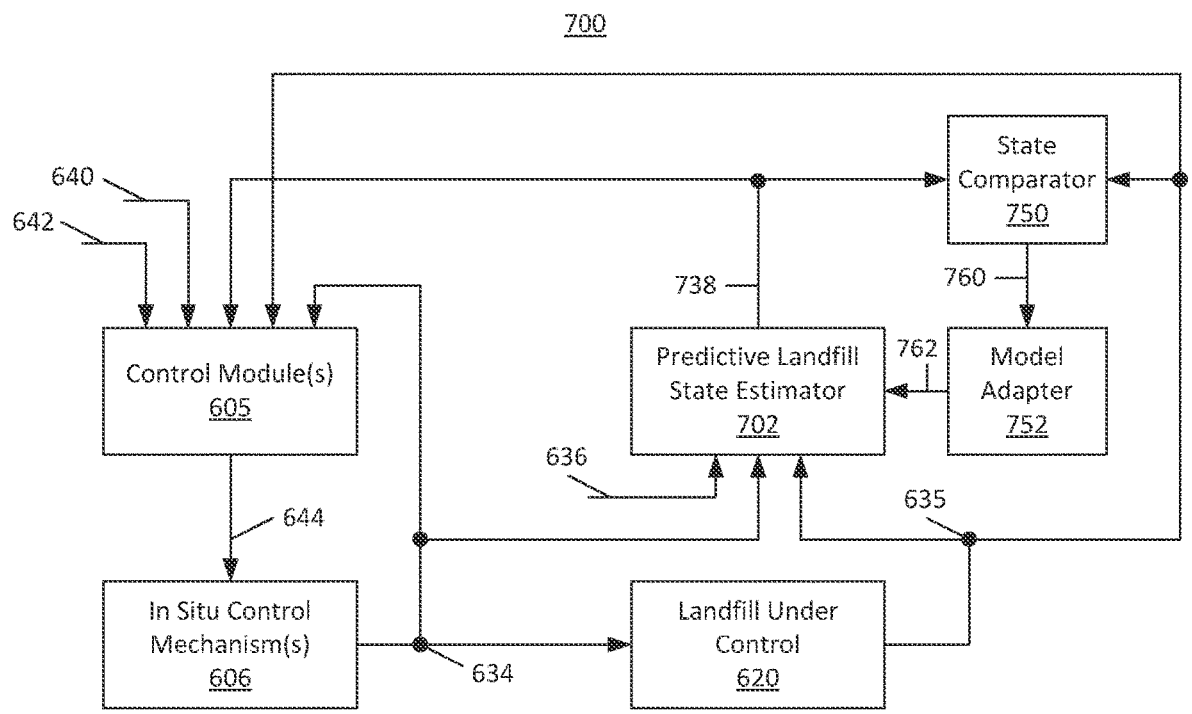
FIG. 7 is a flow diagram illustrating another example of a feedback-based, predictive system for controlling landfill gas extraction, according to some embodiments.

FIG. 7 shows a feedback-based, predictive control system 700, which may be implemented by some embodiments of control system 500 to control the operation of gas extraction system associated with a landfill under control 620. In some embodiments, feedback-based, predictive control system 700 may be adaptive ("self-learning"). In some embodiments of the adaptive control system 700, the predictive landfill state estimator 702 may compare the current state 635 of the landfill (e.g., the current state of landfill gas production) to the previously predicted state 738 of the landfill, and modify parameters in the state estimator's state estimation model or models to make the predicted states more closely match the actual measured states. In this manner, the accuracy of the state estimator's predictions may improve over time, and/or the state estimator may adapt to changing conditions over time, so that the state estimator's predictions remain accurate even as the conditions in and around the landfill change.

In some embodiments, adaptive control system 700 may include a predictive landfill state estimator 702, a state comparator 750, and a model adapter 752. In some embodiments, predictive landfill state estimator 702 may include one or more predictive models of the landfill under control 620, and may apply the predictive model(s) to suitable input data (e.g., current state 634 of flow-control mechanisms, current state 635 of the landfill under control, and/or environmental data 636) to predict one or more future states 738 of the landfill under control.

In some embodiments, state comparator 750 and model adapter 752 may adapt the state estimator's predictive model(s) to improve the accuracy of the predictive model(s). In some embodiments, state comparator 750 may compare a predicted future state 738 of the landfill and a subsequently measured current state 635 of the landfill. In some embodiments, model adapter 752 may use the difference 760 between the predicted state and the actual state of the landfill to determine modified parameter values 762 for one or more parameters in the state estimator's predictive model(s), to improve (e.g., continually improve) the accuracy of those models.

In some embodiments, the modified parameter values 762 output by the model adapter 752 may act to reduce the difference between the predicted future state of the landfill (if it were recalculated using the modified parameter values) and the actual current state of the landfill (e.g., to reduce the difference to zero). In some embodiments, the modified parameter values 762 may act to reduce (e.g., minimize) another error metric (e.g., to reduce the mean error, the sum of the squares of errors for one or more (e.g., all) previous predictions, and/or any other metric). The modified parameter values 762 may be output after every cycle of the feedback loop, or they may be selectively applied. In some embodiments, the model adapter 752 may detect anomalous data points in the measured current state 635 of the landfill (as may happen, e.g., during natural events (e.g., extreme weather), during equipment malfunction (e.g., sensor or control valve failures), when the operations of the Landfill Gas to Energy plant are suddenly disrupted, etc.). In some embodiments, control system 700 may not apply modified parameter values 762 to the predictive model(s) of the predictive landfill state estimator 702 during such events.

In some embodiments, adaptive control system 700 may also include one or more control module(s) 605 and one or more in situ control mechanism(s) 606, which may control the operation of a gas extraction system associated with landfill under control 620. Some embodiments of control module(s) 605 and in situ control mechanism(s) 606 are described above with reference to FIG. 6. For brevity, these descriptions are not repeated here.

Returning to the control system 500 shown in FIG. 5, in some embodiments the controller module 504 may be in communication with a database 510 and/or a user interface 508. In some embodiments, the database 510 may be implemented on a centralized storage mechanism (hard drive, disk drive, or some other non-volatile memory), or it may reside on a distributed storage mechanism (e.g., a cloud server, or any other suitable distributed storage device). The database 510 may serve as a long term archive of historical data and/or past predictions from the predictive landfill state estimator 602, and/or may store past design constraints 640, current design constraints 640, past set points 642, current set points 642, any parameters from the state estimator's predictive model(s), any parameters from the flow-control mechanisms, and/or any other data (for example, environmental data, data from landfill operations, etc.). In some embodiments, the data stored in database 510 may be used to train predictive landfill state estimator 702. In some embodiments, the data stored in database 510 may be provided as input data to the predictive landfill state estimator, which may use the data to predict the next state of the landfill under control. In some embodiments, the data stored in database 510 may be provided as input data to the control module(s) 605 and may be used to determine the values of control parameters 644. The database may be implemented using MySQL, dBASE, IBM DB2, LibreOffice Base, Oracle, SAP, Microsoft SQL Server, MariaDB, SQLite, FoxPro, and/or any other commercially available database management software that will be recognized by one of ordinary skill in the art. In some embodiments, the database may be of a custom construction.

In some embodiments, the controller module 504 may display certain data and/or accept inputs via a user interface 508. In some embodiments, the user interface 508 may include a web site, may include a mobile application (tablet, phone, or other mobile device), and/or may be provided through a terminal via a local network (e.g., secure local network) operating at the landfill under control. The user interface may display current and/or historical gas extraction data collected from a particular well or any set of wells in a given landfill. The user interface may display data via tables, charts, graphs, and/or any other suitable technique, and may do so over various periods of time (e.g., the previous day, past week, past month, etc.). The user interface may overlay data from wells in a given landfill on top of or embedded into aerial maps or renderings of the landfill, and/or it may display data overlays with topographical maps, schematics of the underground piping system, and/or other engineering drawings.

In some embodiments, the user interface may allow users to click on a particular well or set of wells and manually adjust set points, design constraints, and/or other parameters of the control system 500 as they pertain to those wells. The user interface may allow users to set alarms or notifications if gas extraction data or gas data from wells under control cross certain thresholds as defined by the user (for example, a user may request an email or SMS message to be sent in the event that gas from any well exceeds 55% methane or drops below 45% methane by volume, and/or a user may set an alarm if gas temperature rises above 120 degrees Fahrenheit at any well, etc.).

In some embodiments, control modules 605 corresponding to two or more In Situ Control Mechanisms 606 may be in communication with each other (e.g., control modules 605 may be implemented by controller 504 and share data through the memory of controller 504, and/or control modules 605 may be implemented by the corresponding In Situ Control Mechanisms, which may communicate with each other directly or through controller 504). The control parameters 644 for a given In Situ Control Mechanism 606 may then be determined in accordance with, and/or driven by, the behavior, control parameters, sensor readings, and/or other data of other In Situ Control Mechanisms in the landfill under control (e.g., in the surrounding area). Such interdependence among the control parameters 644 of the in situ control mechanisms 606 may improve the performance of the gas extraction system, because adjustments to each gas extraction point, being in fluid communication in the trash, and/or in fluid communication through the gas extraction piping system, may influence the surrounding areas. The spatial area around a given landfill gas extraction well that is affected by that well is called its' "Zone of Influence."

Figure 8:
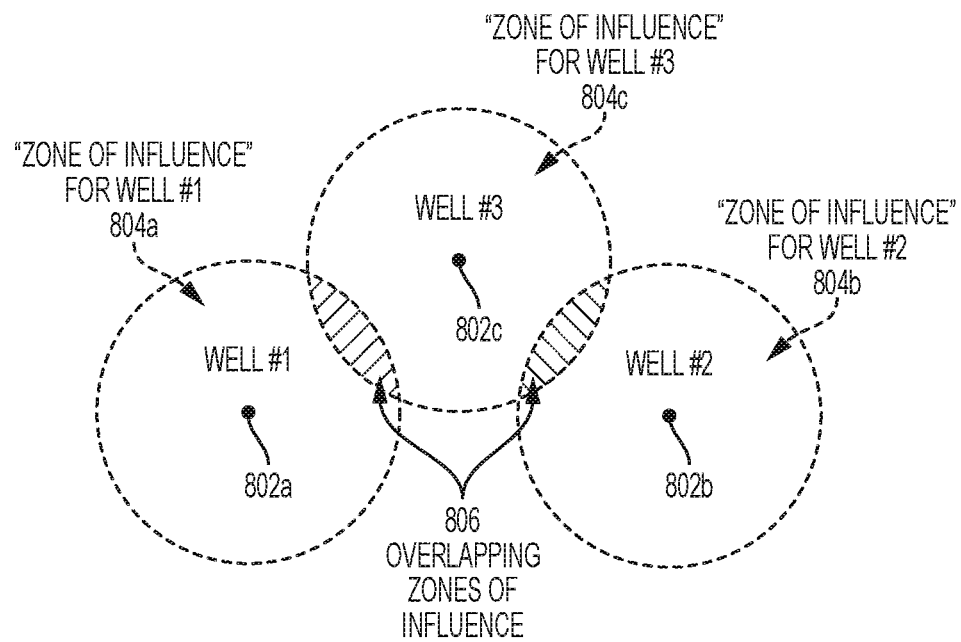
FIG. 8 is a sketch of an example of zones of influence of wells in a landfill.

FIG. 8 depicts the Zones of Influence 804*a-c* around a set of several gas extraction wells 802*a-c*. In this example, well 802*c* has overlapping zones of influence 806 with both other wells. In such an example, changes to the gas extraction rate at well 802*c* will impact the gas characteristics at wells 802*a* and 802*b*. In some embodiments of the landfill gas extraction control system disclosed herein, one objective of the processing performed by the state estimator and/or control module(s) 605 may be to identify such overlapping zones of influence and incorporate interactions between wells into their models.

Figure 9:
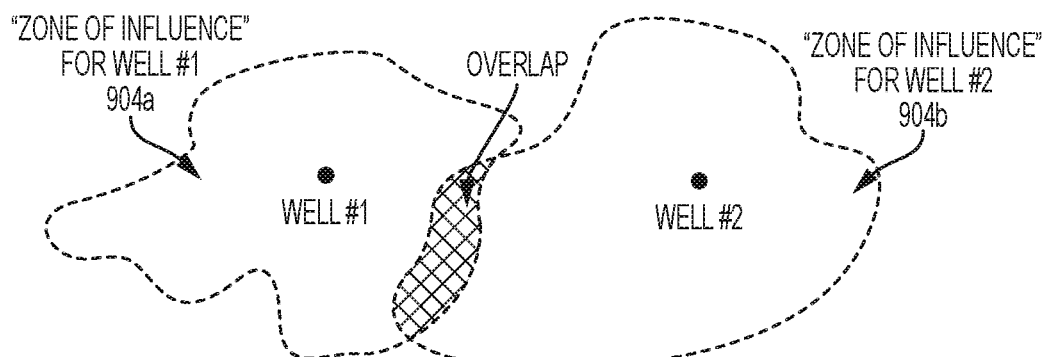
FIG. 9 is a sketch of another example of zones of influence of wells in a landfill.

The inventors have recognized and appreciated that as the porosity of waste in a landfill varies (due to heterogeneous waste composition and compaction at the time of dumping, and also due to the natural decomposition of waste over time and settling effects), certain wells may have highly irregular zones of influence 904*a-b* as depicted in FIG. 9 below. By placing a set of In-Situ Control Mechanisms on adjacent wells in a landfill, it may be possible to quantify and model the strength of interactions between individual wells and to create an interaction matrix that captures an effective "coupling parameter" between any two or more wells in that landfill. In some embodiments, the coupling parameters and/or the interaction matrix may be used to develop or improve the model(s) of the state estimator and/or control module(s) 605 in the control system, and/or may be used to inform the placement of additional wells (e.g., in areas of the landfill where gas extraction may be lacking with the existing wells).

The techniques and devices disclosed herein may be used to modulate the rate of gas extraction of a well or set of wells in accordance with any suitable control scheme, including but not limited to:

Modulation of the gas extraction rate to control vacuum pressure (e.g., maintain and/or obtain a constant vacuum pressure) in the landfill and/or wells under control (in spite of varying atmospheric pressure, temperature, and/or varying rates of gas generation, etc.);

Modulation of the gas extraction rate to maintain and/or obtain a constant flow rate of landfill gas from the landfill and/or wells under control;

Modulation of the gas extraction rate to control (e.g., increase or decrease) the flow rate of landfill gas from the landfill and/or wells under control;

Modulation of the gas extraction rate to maintain and/or obtain a constant percentage of any of the constituent gases (including but not limited to methane, carbon dioxide, oxygen, nitrogen, etc.) in the landfill gas coming from the landfill and/or wells under control;

Modulation of the gas extraction rate to control (e.g., increase or decrease) the concentration of any of the constituent gases in the landfill gas coming from the landfill or wells under control;

Modulation of the gas extraction rate to control (e.g., increase or decrease) the energy content of the landfill gas (e.g., control the total quantity of methane extracted in a given period of time, etc.) coming from the landfill and/or wells under control;

Modulation of the gas extraction rate to control (e.g., increase or decrease) the total volume of the landfill gas (e.g., control the total quantity of landfill gas extracted in a given period of time, etc.) coming from the landfill and/or wells under control;

Modulation of the gas extraction rate to increase the rate of extraction during periods of increased energy demand (e.g., increasing generation during the peaks of real time, hourly, daily, weekly, monthly, and/or seasonal electricity prices);

Modulation of the gas extraction rate to decrease the rate of extraction during periods of reduced energy demand (e.g., reducing generation during the lows of real time, hourly, daily, weekly, monthly, or seasonal electricity prices);

Modulation of the gas extraction rate to control (e.g., maintain, improve, and/or establish) the long term stability of the biochemical decomposition processes (aerobic or anaerobic digestion, etc.) occurring within a section of waste that is in the vicinity of the well(s) under control;

Modulation of the gas extraction rate to control (e.g., increase or decrease) the rates of decomposition occurring within a section of waste that is in the vicinity of the well(s) under control;

Modulation of the gas extraction rate to match the operating parameters or limitations of the gas collection system for the landfill and/or wells under control (including limitations of header junctions and/or subsections of underground piping that impact only certain wells);

Modulation of the gas extraction rate to prevent or extinguish underground fires and/or other potentially dangerous events occurring within a section of waste that is in the vicinity of the well(s) under control;

Modulation of the gas extraction rate to control (e.g., reduce) emission of odors from the landfill and/or wells under control;

Modulation of the gas extraction rate to control (e.g., reduce) emissions of landfill gas or components of landfill gas ($H_2S$, methane, etc.) in the vicinity of the gas extraction well(s) under control;

Modulation of the gas extraction rate to control (e.g., reduce) gas losses into the atmosphere;

Modulation of the gas extraction rate to control (e.g., maintain, improve, and/or establish) compliance of the gas extraction system with local, state and/or federal regulations;

Modulation of the gas extraction rate to control (e.g., reduce) damage to an engine, turbine, and/or other energy generation equipment from contaminants emanating from the vicinity of a well or wells under control;

The success or failure of the above-described control schemes may be assessed in any suitable way. In some embodiments, attributes of the landfill gas may be monitored over a period of time, and a determination may be made as to whether the monitored values comply with the control scheme. For example, to determine whether a specified quantity of methane has been extracted from the landfill in a specified time period, the concentration of methane in the extracted landfill gas and the flow rate of the extracted landfill gas may be monitored during the time period, and quantity of extracted methane may be determined based on the monitored methane concentration levels and gas flow rates. In some embodiments, attributes of the landfill gas may be measured at a specified time, and a determination may be made as to whether the measured values comply with the control scheme. For example, to determine whether the flow rate of extracted landfill gas matches a target flow rate, the flow rate of extracted landfill gas may be measured at some time and compared to the target flow rate.

In some embodiments, the control system 500 may be used to monitor the effect of other treatments besides just the setting of the control valve (e.g., monitoring effects of microbial treatment, leachate recirculation, watering out/ pumping of the wells, adding iron, $H_2S$ abatement, etc.).

Figure 10:
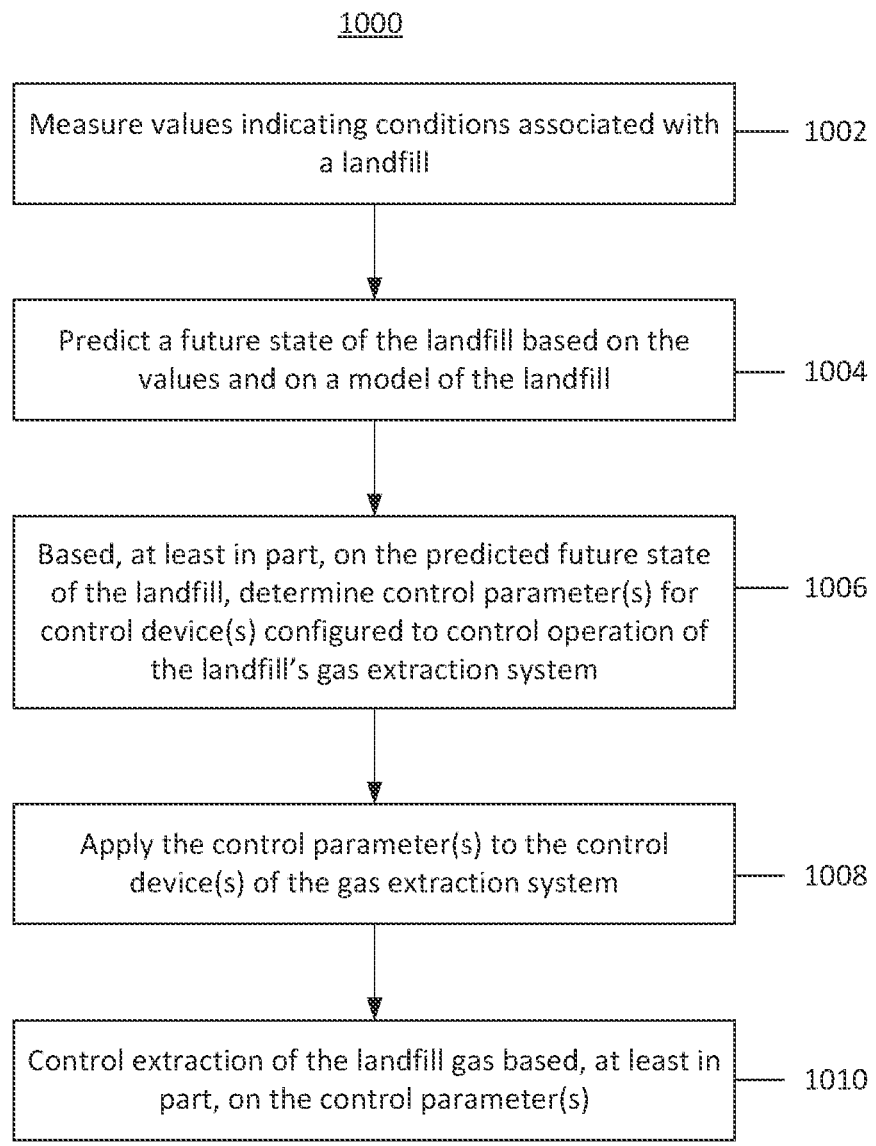
FIG. 10 is a flowchart of a method for controlling extraction of landfill gas from a landfill through a gas extraction system, according to some embodiments.

FIG. 10 illustrates a method 1000 for control extraction of landfill gas from a landfill through a gas extraction system, according to some embodiments. In step 1002 of method 1000, values indicating conditions associated with the landfill are measured. In step 1004 of method 1000, a future state of the landfill is predicted based, at least in part, on the measured values and on the model of the landfill. In some embodiments, the predicted future state may be computed by at least one computing device. In step 1006 of method 1000, one or more control parameters are determined for one or more control devices configured to control operation of the landfill's gas extraction system. In step 1008 of method 1000, the control parameter(s) are applied to the control device(s) of the gas extraction system. In step 1010 of method 1000, extraction of the landfill gas is controlled (e.g., by the one or more control devices) based, at least in part, on the control parameter(s).

In some embodiments, the predicted future state of the landfill may include one or more predicted attributes of the landfill gas produced by the landfill and/or extracted by the gas extraction system at a future time and/or in a future time period. In some embodiments, the future state of the landfill may be predicted based, at least in part, on the predicted future state of the landfill, on the model of the landfill, on the current state of the landfill, on control parameter(s) applied to the control device(s) before making the prediction, and/or on environmental data indicating environmental conditions associated with the landfill. In some embodiments, the current state of the landfill may include the measured values indicating conditions associated with the landfill. In some embodiments, the measured values may be measured by sensor devices (e.g., sensor devices associated with one or more in situ control mechanisms). The values indicating conditions associated with the landfill may include temperature, pressure, flow rate, humidity, density, and/or composition of the landfill gas. In some embodiments, the determined attributes may correspond to landfill gas provided by a single well, landfill gas provided by a plurality of wells, and/or landfill gas extracted from the landfill. In some embodiments, the environmental data may indicate atmospheric pressure, ambient temperature, wind direction, wind speed, characteristics of ambient precipitation, subsurface temperature, subsurface moisture level, and/or pH value of an area of the landfill or adjacent to the landfill.

In some embodiments, the one or more control parameters may be determined based, at least in part, on predicted future electrical power demand and/or on an energy content of the landfill gas extracted from the landfill. In some embodiments, the one or more control parameters may be applied to the one or more respective control devices in real time. In some embodiments, controlling extraction of the landfill gas from the landfill may include controlling a flow rate and/or composition of the landfill gas extracted from the landfill. In some embodiments, the control parameter(s) may be determined based, at least in part, on the predicted future state of the landfill, on a current state of the landfill, on one or more current values of the control parameters, and/or on a control objective for the landfill. In some embodiments, the control parameter(s) may be determined based, at least in part, on electrical power data including past electrical power consumption, past electrical power prices, predicted future electrical power demand, and/or predicted future electrical power prices. In some embodiments, the control parameter(s) may be determined based, at least in part, on a target rate at which the landfill gas is extracted from the landfill by the gas extraction system, a target vacuum pressure applied to the gas extraction system, a target composition of the landfill gas extracted from the landfill by the gas extraction system, a target energy content of the landfill gas extracted from the landfill by the gas extraction system, a target volume of the landfill gas extracted from the landfill by the gas extraction system, a target stability of a decomposition process in the landfill, a target rate of a decomposition process in the landfill, a target rate of emission of the landfill gas into an atmosphere, a target odor level associated with emission of the landfill gas into the atmosphere, and/or a target level of compliance with one or more regulations applicable to the landfill.

Although not illustrated in FIG. 10, some embodiments of method 1000 may include one or more steps for adapting the predictive model(s) of the predictive landfill state estimator. In some embodiments, such steps may include (1) after computing the predicted future state of the landfill at the future time, determining an actual state of the landfill at the future time, and (2) adapting the model based, at least in part, on a difference between the predicted future state of the landfill and the determined actual state of the landfill. In some embodiments, adapting the model may include adapting the model to decrease the difference between the predicted future state of the landfill and the determined actual state of the landfill.

Figure 11:
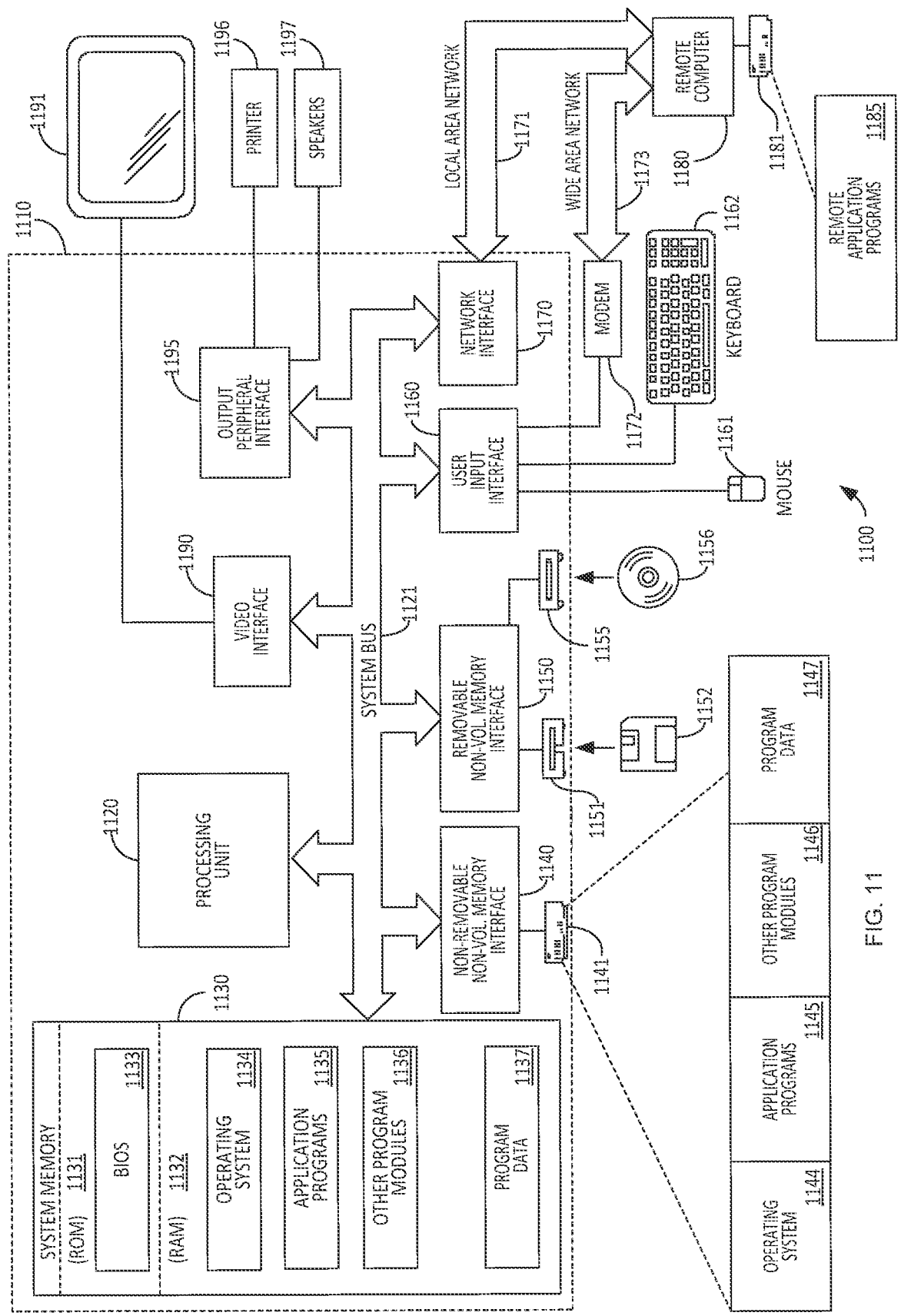
FIG. 11 is a block diagram of an exemplary computer system in which aspects of the present disclosure may be implemented, according to some embodiments.

FIG. 11 illustrates an example of a suitable computing system environment 1100 on which techniques disclosed herein may be implemented. In some embodiments, portions of a landfill gas extraction control system may be implemented in a computing system environment. For example, in some embodiments, Device Manager 502, Controller Module 504, User Interface 508, and/or Database 510 may be implemented in a computing system environment. In some embodiments, aspects of one or more techniques describes herein may be implemented in a computing system environment.

The computing system environment 1100 is only one example of a suitable computing environment and is not intended to suggest any limitation as to the scope of use or functionality of the devices and techniques disclosed herein. Neither should the computing environment 1100 be interpreted as having any dependency or requirement relating to any one or combination of components illustrated in the exemplary operating environment 1100.

The techniques disclosed herein are operational with numerous other general purpose or special purpose computing system environments or configurations. Examples of well-known computing systems, environments, and/or configurations that may be suitable for use with techniques disclosed herein include, but are not limited to, personal computers, server computers, hand-held devices (e.g., smart phones, tablet computers, or mobile phones), laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 11, an exemplary system for implementing techniques described herein includes a general purpose computing device in the form of a computer 1110. Components of computer 1110 may include, but are not limited to, a processing unit 1120, a system memory 1130, and a system bus 1121 that couples various system components including the system memory to the processing unit 1120. The system bus 1121 may be any of several types of bus structures including a memory bus or memory controller, a peripheral bus, and/or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1110 typically includes a variety of computer readable media. Computer readable media can be any available media that can be accessed by computer 1110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1130 includes computer storage media in the form of volatile and/or nonvolatile memory such as read only memory (ROM) 1131 and random access memory (RAM) 1132. A basic input/output system 1133 (BIOS), containing the basic routines that help to transfer information between elements within computer 1110, such as during start-up, is typically stored in ROM 1131. RAM 1132 typically contains data and/or program modules that are immediately accessible to and/or presently being operated on by processing unit 1120. By way of example, and not limitation, FIG. 11 illustrates operating system 1134, application programs 1135, other program modules 1136, and program data 1137.

The computer 1110 may also include other removable/non-removable, volatile/nonvolatile computer storage media. By way of example only, FIG. 11 illustrates a hard disk drive 1141 that reads from or writes to non-removable, nonvolatile magnetic media, a magnetic disk drive 1151 that reads from or writes to a removable, nonvolatile magnetic disk 1152, and an optical disk drive 1155 that reads from or writes to a removable, nonvolatile optical disk 1156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1141 is typically connected to the system bus 1121 through an non-removable memory interface such as interface 1140, and magnetic disk drive 1151 and optical disk drive 1155 are typically connected to the system bus 1121 by a removable memory interface, such as interface 1150.

The drives and their associated computer storage media discussed above and illustrated in FIG. 11, provide storage of computer readable instructions, data structures, program modules and other data for the computer 1110. In FIG. 11, for example, hard disk drive 1141 is illustrated as storing operating system 1144, application programs 1145, other program modules 1146, and program data 1147. Note that these components can either be the same as or different from operating system 1134, application programs 1135, other program modules 1136, and program data 1137. Operating system 1144, application programs 1145, other program modules 1146, and program data 1147 are given different numbers here to illustrate that, at a minimum, they are different copies. A user may enter commands and information into the computer 1110 through input devices such as a keyboard 1162 and pointing device 1161, commonly referred to as a mouse, trackball or touch pad. Other input devices (not shown) may include a microphone, joystick, game pad, satellite dish, scanner, or the like. These and other input devices are often connected to the processing unit 1120 through a user input interface 1160 that is coupled to the system bus, but may be connected by other interface and bus structures, such as a parallel port, game port or a universal serial bus (USB). A monitor 1191 or other type of display device is also connected to the system bus 1121 via an interface, such as a video interface 1190. In addition to the monitor, computers may also include other peripheral output devices such as speakers 1197 and printer 1196, which may be connected through a output peripheral interface 1195.

The computer 1110 may operate in a networked environment using logical connections to one or more remote computers, such as a remote computer 1180. The remote computer 1180 may be a personal computer, a server, a router, a network PC, a peer device or other common network node, and typically includes many or all of the elements described above relative to the computer 1110, although only a memory storage device 1181 has been illustrated in FIG. 11. The logical connections depicted in FIG. 11 include a local area network (LAN) 1171 and a wide area network (WAN) 1173, but may also include other networks. Such networking environments are commonplace in offices, enterprise-wide computer networks, intranets and the Internet.

When used in a LAN networking environment, the computer 1110 is connected to the LAN 1171 through a network interface or adapter 1170. When used in a WAN networking environment, the computer 1110 typically includes a modem 1172 or other means for establishing communications over the WAN 1173, such as the Internet. The modem 1172, which may be internal or external, may be connected to the system bus 1121 via the user input interface 1160, or other appropriate mechanism. In a networked environment, program modules depicted relative to the computer 1110, or portions thereof, may be stored in the remote memory storage device. By way of example, and not limitation, FIG. 11 illustrates remote application programs 1185 as residing on memory device 1181. It will be appreciated that the network connections shown are exemplary and other means of establishing a communications link between the computers may be used.

Embodiments of the above-described techniques can be implemented in any of numerous ways. For example, the embodiments may be implemented using hardware, software or a combination thereof. When implemented in software, the software code can be executed on any suitable processor or collection of processors, whether provided in a single computer or distributed among multiple computers. In some embodiments, the functions performed by an In Situ Control Mechanism 106 and/or a Controller 204 may be implemented as software executed on one or more processors.

Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various events/acts are described herein as occurring or being performed at a specified time. One of ordinary skill in the art would understand that such events/acts may occur or be performed at approximately the specified time.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

What is claimed is:

1. A system for controlling extraction of landfill gas from a landfill via a gas extraction system, the system comprising:
    a plurality of in situ control mechanisms, each of the plurality of in situ control mechanisms comprising:
        a gas analyzer; and
        at least one flow control mechanism configured to control flow of landfill gas being extracted from at least one well of the landfill; and
    a device manager communicatively coupled to the plurality of in situ control mechanisms using a star network of wireless data links, wherein:
        the plurality of in situ control mechanisms are configured to communicate to the device manager via the star network of wireless data links, data comprising sensor measurements obtained by the plurality of in situ control mechanisms;
        the device manager is configured to communicate to the plurality of in situ control mechanisms via the star network of wireless data links, commands instructing the plurality of in situ control mechanisms to adjust flow rates of landfill gas being extracted from the landfill, the commands being determined based on the data communicated by the plurality of in situ control mechanisms; and
        the plurality of in situ control mechanisms are configured to adjust the flow rates of the landfill gas being extracted from the landfill responsive to the commands communicated by the device manager.

2. The system of claim 1, wherein the device manager is communicatively coupled to a server.

3. The system of claim 2, wherein the device manager and the server are communicatively coupled via a local area network (LAN) and/or a wide area network (WAN).

4. The system of claim 1, wherein the data comprising sensor measurements comprises measurements of concentration of a constituent gas in landfill gas extracted from the landfill.

5. The system of claim 4, wherein the constituent gas is methane.

6. The system of claim 4, wherein the constituent gas is oxygen.

7. The system of claim 1, wherein the data comprising sensor measurements comprises measurements of temperature of landfill gas extracted from the landfill.

8. The system of claim 1, wherein the data comprising sensor measurements comprises measurements of vacuum pressure in the gas extraction system.

9. The system of claim 1, wherein the commands comprise instructions to increase flow rates of landfill gas being extracted from the landfill.

10. The system of claim 1, wherein the commands comprise instructions to decrease flow rates of landfill gas being extracted from the landfill.

11. The system of claim 1, wherein the gas analyzer comprises a chamber and one or more sensors.

12. The system of claim 11, wherein the one or more sensors are disposed within the chamber.

13. A method for controlling extraction of landfill gas from a landfill via a gas extraction system, the method comprising:
    establishing a star network of wireless data links communicatively coupling a plurality of in situ control mechanisms and a device manager, wherein:
        each of the plurality of in situ control mechanisms comprise:
            a gas analyzer; and
            at least one flow control mechanism configured to control flow of landfill gas being extracted from at least one well of the landfill; and
    communicating data from the plurality of in situ control mechanisms to the device manager via the star network of wireless data links, the data comprising sensor measurements obtained by the plurality of in situ control mechanisms;

communicating commands from the device manager to the plurality of in situ control mechanisms via the star network of wireless data links, the commands instructing the plurality of in situ control mechanisms to adjust flow rates of landfill gas being extracted from the landfill, and the commands being determined based on the data communicated by the plurality of in situ control mechanisms; and adjusting the flow rates of landfill gas being extracted from the landfill responsive to the commands communicated by the device manager.

14. The method of claim 13, further comprising establishing a communication connection between the device manager and a server, the communication connection comprising a local area network (LAN) and/or a wide area network (WAN).

15. The method of claim 13, wherein the data comprising sensor measurements comprises measurements of concentration of a constituent gas in landfill gas extracted from the landfill.

16. The method of claim 15, wherein the constituent gas is methane.

17. The method of claim 15, wherein the constituent gas is oxygen.

18. The method of claim 13, wherein the data comprising sensor measurements comprises measurements of temperature of landfill gas extracted from the landfill.

19. The method of claim 13, wherein the data comprising sensor measurements comprises measurements of vacuum pressure in the gas extraction system.

20. The method of claim 13, wherein the gas analyzer comprises a chamber and one or more sensors disposed within the chamber.

* * * * *